United States Patent [19]

Ashmead et al.

[11] Patent Number: 5,690,763

[45] Date of Patent: Nov. 25, 1997

[54] INTEGRATED CHEMICAL PROCESSING APPARATUS AND PROCESSES FOR THE PREPARATION THEREOF

[75] Inventors: James William Ashmead; Charles Thomas Blaisdell, both of Middletown, Del.; Melvin Harry Johnson; Jack Kent Nyquist, both of Chadds Ford, Pa.; Joseph Anthony Perrotto, Landenberg, Pa.; James Francis Ryley, Jr., Drexel Hill, Pa.

[73] Assignee: E. I. Du Pont de Nemours and Company, Wilmington, Del.

[21] Appl. No.: 469,274

[22] Filed: Jun. 6, 1995

Related U.S. Application Data

[60] Division of Ser. No. 161,379, Dec. 2, 1993, Pat. No. 5,534,328, which is a continuation-in-part of Ser. No. 33,915, Mar. 19, 1993, abandoned.

[51] Int. Cl.⁶ .............................................. B31B 1/60
[52] U.S. Cl. ........................ 156/60; 156/252; 156/644.1; 422/1; 422/38; 55/410; 55/413; 55/442; 55/464; 261/110; 210/97; 210/150; 210/294
[58] Field of Search ........................... 156/60, 145, 644.1, 156/87, 252; 261/110; 210/150, 97, 294; 55/410, 413, 442, 464; 165/163, 164, 169; 422/130, 200, 189, 196

[56] References Cited

U.S. PATENT DOCUMENTS

| | | | |
|---|---|---|---|
| 1,662,870 | 3/1928 | Stancliffe | 29/157.3 D |
| 3,701,619 | 10/1972 | Appeldoorn et al. | 425/198 |
| 3,856,270 | 12/1974 | Hemker | 259/4 |
| 4,053,969 | 10/1977 | Bayard | 29/157.3 D |
| 4,222,671 | 9/1980 | Gilmore | 366/337 |
| 4,365,178 | 12/1982 | Lenz | 310/61 |
| 4,383,008 | 5/1983 | Chi | 429/38 |
| 4,390,351 | 6/1983 | Matsui et al. | 55/204 |
| 4,534,659 | 8/1985 | Dourdeville et al. | 366/338 |
| 4,573,067 | 2/1986 | Tuckerman et al. | 357/82 |
| 4,869,849 | 9/1989 | Hirose et al. | 261/78.2 |
| 4,894,709 | 1/1990 | Phillips et al. | 357/82 |
| 4,908,112 | 3/1990 | Pace | 204/299 R |
| 5,177,398 | 1/1993 | Engemann | 313/360.1 |
| 5,209,906 | 5/1993 | Watkins et al. | 422/200 |

FOREIGN PATENT DOCUMENTS

| | | | |
|---|---|---|---|
| 0 347 579 | 12/1989 | European Pat. Off. | B01L 3/00 |
| 2 640 620 | of 1990 | France | C04B 35/74 |
| 39 26 466 | 2/1991 | Germany | B01J 19/24 |
| 680 780 | 11/1992 | Switzerland | C04B 38/00 |
| 2 191 110 | 12/1987 | United Kingdom | B10D 15/08 |

OTHER PUBLICATIONS

Huff et al., "Fabrication, Packaging, And Testing Of A Wafer-Bonded Microvalve", *Mass. Inst. Of Technology*, Abstract 0-7803-0456-X/92, 1992.

Smith et al., "The Design And Fabrication Of A Magnetically Actuated Micromachined Flow Valve", *Sensor And Actuators*, 24, 47-53, 1990.

*Primary Examiner*—Donald Loney

[57] ABSTRACT

An integral structure is provided for chemical processing and manufacture, in which a plurality of laminae are joined together and having inlet and outlet ports connected by a three dimensionally tortuous channel. Chemicals are introduced through the inlet ports and processed along the channel, with desirable product withdrawn through the outlet ports. The laminae are of materials selected to be compatible with the chemical process, from the group consisting of elements of groups III, IV or V of the Periodic Table, ceramics, glasses, polymers, composites and metals. Processes of manufacture of the apparatus and processes utilizing the apparatus are also disclosed herein.

10 Claims, 18 Drawing Sheets

INTEGRATED CHEMICAL PROCESSING APPARATUS AND PROCESSES FOR THE PREPARATION THEREOF

This is a continuation of application Ser. No. 08/161,379, filed Dec. 2, 1993 now U.S. Pat. No. 5,534,328 which is a continuation-in-part of application Ser. No. 08/033,915, filed Mar. 19, 1993 and now abandoned.

FIELD OF THE INVENTION

This invention relates to miniaturized chemical processing apparatus, which integrates chemical processing units into an integral structure and processes of manufacture. More particularly, the present invention is directed to chemical processing apparatus characterized by improved precision of control of the processing parameters for chemicals passing therethrough, by enhanced safety of operation, and by reduced capital investment.

BACKGROUND OF THE INVENTION

To achieve efficient chemical processing and manufacture, it is necessary to precisely control a number of processing parameters, such as temperature, pressure, mixing conditions, exposure of reactants to catalyst material, and exposure of reactants to actinic radiation, as well as conditions to achieve separation of the reaction products.

Conventional processing equipment suffers from a number of disadvantages. It has long been recognized in the chemical industry that "scale up" from laboratory bench scale to commercial production scale is difficult. Results achieved in the laboratory are often difficult to duplicate at production rates in production facilities. The conventional wisdom of "economy of scale" is based upon economic considerations which relate production rate (units of product per unit of time) to capital investment. This conventional approach results in less than optimum precision of control of chemical processing.

Conventional chemical processing equipment typically holds a relatively large volume of materials and consequently has a relatively large volume to surface area ratio. It is therefore likely that different portions of the reactant materials contained within such equipment are exposed to different histories of conditions. In the case of a conventional tank reactor, for example, even when temperature conditions at the walls of the reactor are well controlled, the portions of the reactants that are not in close proximity to the walls of the reactor may experience different temperature histories, especially if a significant temperature gradient exists, which might occur if the chemical reaction is strongly exothermic. Rapid stirring of the reactants may reduce this temperature history difference, but will not eliminate it. As a result of the nonhomogeneous temperature history, different portions of the reactants may chemically react differently. Undesired reactions may occur in portions of the reactants that are exposed to histories of higher than desired temperatures. This may result in the production of undesired waste products, which may be hazardous and which must be properly disposed of. In extreme situations reaction rates may accelerate to uncontrollable levels, which may cause safety hazards, such as potential explosions.

If, however, the volume to surface area ratio of the processing apparatus is substantially reduced, the degree of precision of control of homogeneity of temperature history of the reactants can be substantially improved.

It has been recognized that a high degree of flow turbulence enhances the ability to rapidly mix two or more reactants together. Rapid mixing is important for fast-acting chemical reactions. A high degree of turbulence is also known to enhance heat transfer. Thus, a structure having both a low volume to surface area ratio and a high degree of flow turbulence is particularly advantageous for precise control of chemical processing.

Individual units, such as miniaturized chemical reactors, have been fabricated from a stack of grooved metal plates, as in DE 3,926,466. It is also known to construct heat exchangers from a stack of grooved metal foils or plates or from grooved silicon wafers bonded to glass plates. Fabrication of small precise interior channels in structures, heretofore has been difficult. However, it has been achieved with diamond tipped metalworking machine tools primarily limited to straight channels, due to constraints imposed by the fabrication techniques. Such structures typically have a plurality of closely spaced straight parallel grooves with a manifold at each end of the grooves. Such straight-grooved structures, however, do not achieve the rates of mixing and the degree of turbulence in the mixture flow believed to be necessary for very fast chemical reactions.

Mixer assemblies having highly turbulent flow have been constructed by machining the desired passages and chambers in metal plates, using conventional metalworking techniques, and then assembling the plates into a stack and either clamping the stack together or permanently joining the stack, as by welding or soldering. An example is U.S. Pat. No. 3,701,619. Since conventional machine tool techniques are not well adapted to economically forming complex miniaturized structures, such structures cannot achieve particularly low volume surface area ratios. Such devices are individual units and are not integral structures for chemical processing and manufacture.

The materials of construction of conventional chemical processing apparatus, such as steel and specialty iron alloys, furthermore may be subject to corrosion and wear, may have undesirable effects on catalytic activity, or may "poison" a catalyst. The apparatus of the present invention may be fabricated from a range of materials, selected to be compatible with the chemical process. Some of the specific techniques used to fabricate the apparatus are dependent on the material selected.

The present invention provides the capability to integrate one or more unit operations with sensors and control elements to meet the needs of a specific chemical reaction. A feature of the present invention is that it can be economically used in the laboratory, to make a range of precise sizes of a given element or operation unit, to perform the basic chemical reactions for determining optimum operating parameters for commercial volume production version of the integrated chemical processing unit. An additional feature of the present invention is that it can process multiphase materials. Advantages of the present invention include the elimination of many interconnections and joints, thereby reducing the potential for leaks. These and other objects, features and advantages will become better understood upon having reference to the following description of the invention.

SUMMARY OF THE INVENTION

There is disclosed and claimed herein an integral structure for chemical processing and manufacture comprising a plurality of laminae joined together with at least one inlet port and at least one outlet port formed therein for the receipt and discharge of chemicals. The laminae have at least one three-dimensionally tortuous channel formed therethrough for accommodating chemicals to be processed. The channel, which desirably measures from about 10 to about 5000 micrometers in cross section, connects to the inlet and outlet ports. The laminae comprise a material selected to be compatible with the specific chemical process. Means to perform at least one unit operation are positioned to effect a desired control so that the chemicals are processed.

Exemplary of materials suitable for high temperature oxidation reactions, such as the oxidation of hydrochloric acid (HCl) to produce chlorine (Cl) and water ($H_2O$), are materials from groups III, IV, and V of the Periodic Table, such as silicon. Exemplary of materials found to be suitable for fluorination reactions, such as the fluorination of $CF_3CH_2Cl$ to produce $CF_3CH_2F$, include ceramics, such as silicon carbide, tungsten carbide, alumina and sapphire. Exemplary of materials suitable for photoreactions, such as the photochlorination of dichlorodimethylsilane (DCDMS) are glass materials, such as fused quartz, pure silica glass and borosilicate glass. Exemplary of materials found to be suitable for bioreactions, such as the proteolytic enzymatic conversion of proteins to other substances are polymers, such as polystyrene, polyester, polyamide, and polytetrafluoroethylene polymers. Exemplary of materials suitable for high pressure process conditions are composite materials, such as fiber reinforced polymers and ceramics. Exemplary of materials suitable for less demanding process conditions are metals.

In a preferred embodiment of the integral structure the laminae are arranged to accommodate a plurality of unit operations. In addition, the channel is precisely oriented between adjacent laminae. These channels may be continuous or discontinuous along said laminae thereof. Discontinuous channels are continuously aligned between adjacent laminae sufficient to form a continuous pathway therethrough.

The integral structure of the invention may be prepared according to the following process, comprising:

(a) first processing a plurality of laminae each having a top portion and a bottom portion and a desired thickness, sufficient to form desired pathways thereon or therethrough.

(b) The laminae are stacked and bonded together in precise alignment to include at least one inlet port and at least one outlet port formed therein for the receipt and discharge of chemicals. The pathways form at least one three-dimensionally tortuous channel therethrough for accommodating chemicals to be processed. This channel, which desirably measures from about 10 to about 5000 micrometers in cross section, connects to the inlet and outlet ports. The laminae comprise a material selected to be compatible with the specific chemical process.

(c) Finally, one or more means to perform at least one unit operation are positioned to effect a desired control so that the chemicals are processed.

The processing of the laminae to form pathways may be performed by a procedure selected from the group of: subtractive processes, comprising chemical etching (such as used to process wafers of semiconductor material), electrochemical machining (ECM), electrical discharge machining (EDM), laser ablation, drilling and cutting, abrasive grinding and single diamond point cutting (such as used to fabricate ceramic parts); additive processes, comprising deposition processes, such as electroforming, selective plating, chemical vapor deposition, stereo lithographic photoforming, and welding; and forming processes, such as molding, casting, and stamping. Wear resistant coatings, in the form of thin films, may be optionally deposited on the processed laminae before bonding.

In the process for preparing the integral structure, the pathways on facing surfaces of adjacent laminae form passages through the structure in the plane of the laminae having the desired cross-sectional areas. These planar passages are connected with each other and with passages orthogonal to the plane of the laminae which pass through one or more laminae to form passages having the desired overall three-dimensional tortuous shapes. The term "three-dimensional tortuous," as used herein, is intended to include the characteristic that the passages may be bifurcated, branched, intersecting or reentrant, and may be of constant or varying cross-sectional shape and size to achieve the desired flow characteristics of chemicals to be passed therethrough.

The above-described apparatus may be used in a method for chemical processing and manufacture. The method comprises:

(a) introducing one or more chemicals to be processed into the inlet port of the above-described structure.

(b) directing the one or more chemicals to traverse at least one tortuous channel that is specially adapted to receive the one or more chemicals.

(c) coordinating the traversal of the one or more chemicals through the tortuous channel with means that perform at least one of the following unit operations to the one or more chemicals:
   A—mixing,
   B—heat exchanging,
   C—separating,
   D—reacting catalytically,
   E—reacting noncatalytically,
   F—reacting photochemically, and
   G—reacting electrochemically.

(d) withdrawing one or more processed chemicals from the outlet port. This processing is characterized by coordination of the design of the tortuous channel with the unit operations effected upon the one or more chemicals being processed.

Each of these unit operations may be performed individually or in conjunction with other unit operations in the same or in different apparatus. The structures of this invention are specially suited for continuous or semi-continuous operations.

The invention can be more fully understood from the following detailed description thereof in connection with accompanying drawings described as follows.

DETAILED DESCRIPTION OF THE INVENTION

It is characteristic of the apparatus of this invention that it can readily be adapted to effect all or nearly all chemical reactions that one may conceive. Depending on the physical and chemical properties of the individual chemicals being processed, or the two or more chemicals being reacted, one skilled in the art can design an apparatus having the requisite size, shape and throughput of tortuous channel and the number, and geometry, of the various laminae. The type and location of unit operation means can be adapted to the designed apparatus and integrated therewith. Finally, if desired, an array of apparatuses can be joined in sequential and/or tandem operation. Because of the materials of construction, convenient size and adaptability of the integrated structure of this invention, one may begin pilot plant or commercial operation of a target process more quickly, with greater flexibility, fewer start-up difficulties and utilizing low capital overhead investment than heretofore. This is all possible because of the special adaptability of the structures and design parameters to effect nearly any chemical process.

The present invention is characterized by small channels of complex three-dimensional shapes which: (1) can create a high degree of flow turbulence that enhances mixing and heat transfer; (2) have a very low volume to surface area ratio that minimizes temperature gradients and further enhances heat transfer; and (3) controls residence time of materials therein, to achieve more precise temperature control, and a more uniform temperature history, for every portion of the entire volume of reactants processed. Channels small enough that they will not allow the propagation of a flame may be readily formed and thus can be used to safely react potentially explosive chemical reactants.

The structure of the present invention is achieved by a multi-step fabrication process. First, a series of planar laminae or wafers, are processed to form desired patterns of pathways on one or both major surfaces of each lamina or through the thickness of the lamina. Selection of lamina materials is dependent on compatibility with the chemical process. As used herein the term "compatibility with the chemical process" includes: resistance to chemical degradation; operating conditions, such as temperature and pressure; thermal conduction requirements; required features to be created in the lamina, including size, geometrical shape and precision; the sealability of the lamina material; and economic considerations. For example, wafers similar to those used to fabricate semiconductor electronics components, such as single crystal silicon wafers, may be used. For materials such as silicon a combination of techniques, including chemical etching, such as used to process wafers of semiconductor material, and laser drilling and cutting, such as used to fabricate ceramic parts, may be used to form the passages.

Figure 1:
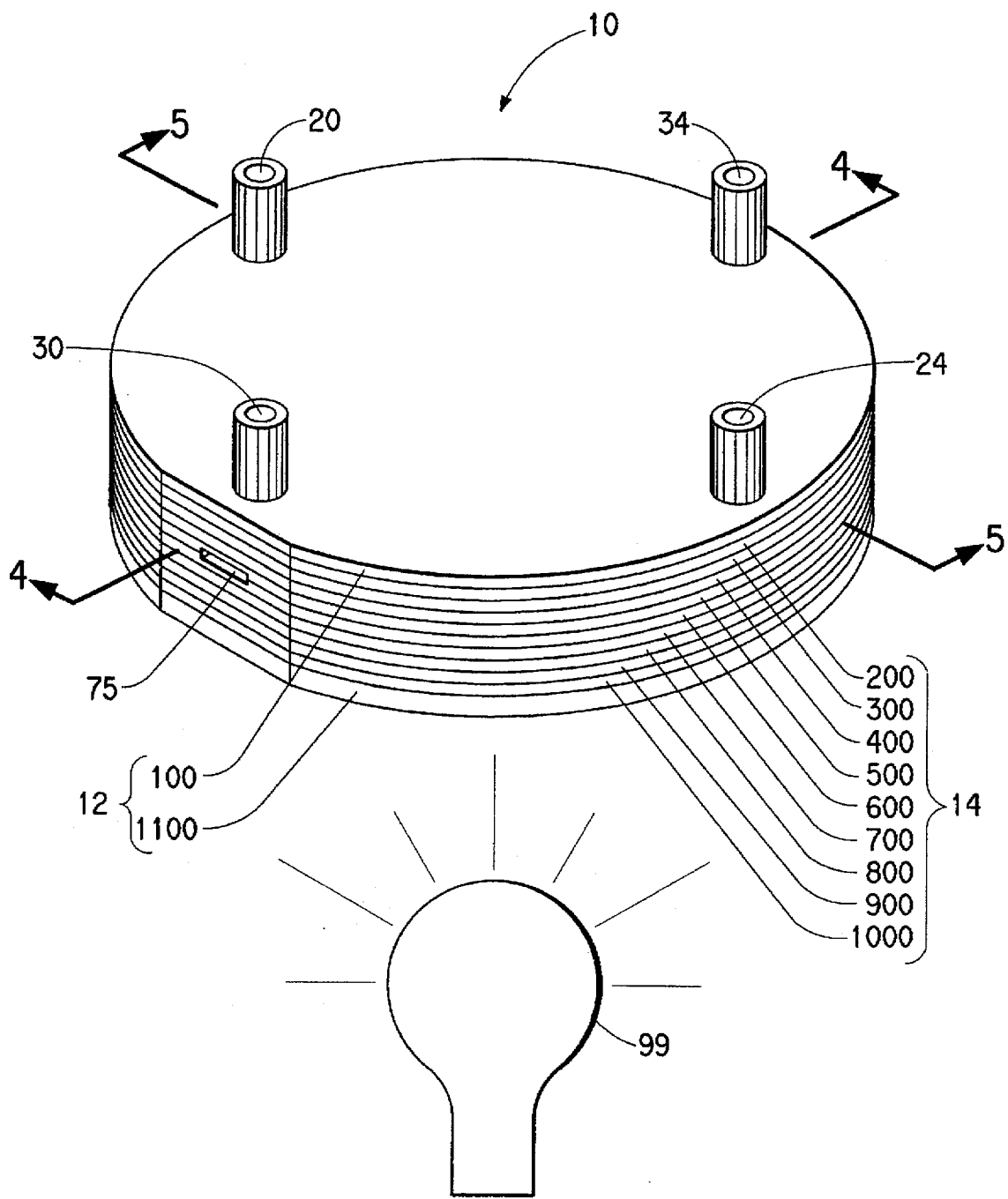
FIG. 1 is a perspective view of an apparatus of the present invention.

The laminae are subsequently stacked in precise alignment and joined together (as by, for example, thermal fusion bonding; anodic bonding, adhesive bonding, alloy bonding, and clamping) into an integral structure. By "plurality" of laminae as is claimed herein it is understood that the integrated structure may consist of as few as two laminae or more laminae, suitably joined. As illustrated in the example of FIG. 1, eleven laminae are joined as an apparatus, with the first and last laminae forming an outer group and the remaining laminae forming an inner group. The outer group may be silicon or a protective material such as metal, ceramic, composite material or glass while the inner group might be silicon. Thermal fusion bonding is a preferred method of joining the laminae if the inner group is made of silicon because the strength of the bond achieved approaches that of the laminae themselves.

The present invention preferably uses materials selected to be compatible with the specific chemical process. Materials of groups III, IV and V of the Periodic Table, most preferably materials of group IVA, and still most preferably silicon and germanium, have been found to be compatible with a number of chemical processes. For certain chemical processes silicon and similar materials have numerous advantages over conventional reactor materials such as steel and specialty metal alloys and are especially resistant to corrosion and wear. If needed, surface layers such as silicon oxide, silicon nitride, silicon carbide or synthetic diamond may be formed on the laminae, which will increase the resistance to corrosion and wear.

Silicon and similar materials have high thermal conductivity that enhances heat distribution and promotes uniform temperatures. Silicon has a relatively low coefficient of thermal expansion and tolerates large temperature gradients and rapid temperature changes. The high thermal conductivity and tolerance to large temperature gradients may be exploited by forming evacuated chambers within the structure to create thermal barriers, and maintaining different parts of the integrated unit at different temperatures. Thus, incoming chemical reactants may, for instance, be mixed at a low temperature, rapidly heated and completely reacted and then rapidly cooled to prevent formation of undesired compounds or thermal degradation of the desired product.

An ample supply of high quality materials and a long history of well developed processing techniques is available, as used within the semiconductor electronics industry. The unique ability to fusion bond silicon and other group III, IV and V materials to form a multilayer solid, leak proof monolithic structure facilitates economical fabrication of complex chemical processing apparatus, which are both compact and intrinsically safe, from a plurality of simple wafers.

As used herein, apparatus to perform "unit operations" includes mixers, flow distribution channels, heat exchangers, separators, and reaction chambers, including catalytic and non-catalytic, photochemical, electrochemical, and like types.

Means to control unit operations, can be combined in the present integral structure with process monitors, such as pressure sensors, temperature sensors, flow sensors, and chemical composition sensors and with control devices, such as valves, pumps, and heaters/coolers to effectively control the processing parameters. Such means perform a specific function (alone or in combination with other means) as desired on chemicals. One such example is separation with integral temperature control. Integration of all of the operations into a single chemical processing unit provides additional advantages, such as: more precise control of operating parameters than in prior systems; reducing path lengths, thus reducing opportunities for degradation of the chemicals; and utilizing the heat of reactions to preheat incoming materials, thus reducing energy requirements. In addition, the means to perform the unit operations are not necessarily secured to the integral structure. Such means could, for example, be external to the structure such as using a water bath as temperature control means.

Materials may be selected for their lack of catalytic activity and relative inertness for the chemical process of interest. Catalysts having the desired activity may then be readily incorporated into the integrated chemical processing unit.

Typical means to incorporate catalytic activity into the integrated structure is to pack a segment of a channel with catalytic beads or deposit catalytic materials onto the surface of a channel. There are various techniques available to those skilled in the art to accomplish such a unit operation.

The fabrication method described in the example of the present invention allows for simple, mass production of precise, complex shaped channels or other structures in a material that is uniquely suited for chemical processing equipment. The fabrication method facilitates precise replication of critical features so that larger amounts of chemicals may be processed by simply replicating the features as many times as necessary to achieve the desired production rate of chemicals processed. By placing the operations necessary for a given process in a compact, integrated structure, further increased volume production of a given chemical becomes simply a matter of replicating or scaling-out the integrated chemical processing unit and operating the replicated units in parallel. As opposed to scaling up large multi-liter tanks currently used in conventional chemical processing, this invention provides greater flexibility for phased investment and small distributed processing plants by scaling-out by replication. Making chemicals on demand at the location of consumption holds the potential of eliminating shipping and handling hazards associated with centralized manufacturing and distribution of hazardous chemicals.

Safety is enhanced in several ways when only small volumes of materials are processed in small reactor elements. The small size of the channels prevent the propagation of flames and thus greatly reduce or eliminate the potential for an explosion, and the total volume of chemical material within the apparatus is small which reduces the magnitude of potential spills or explosions. This creates the potential to safely perform certain chemistries on a commercial scale that previously could not be performed safely using traditional processing approaches. The ability to more precisely control the chemical reaction by the use of small precise reactors also minimizes the potential of undesirable side reactions which create waste and lead to fouling of the chemical processing unit. The present invention thus increases productivity and reduces hazards.

Throughout the following detailed description, similar reference characters refer to similar elements in all figures of the drawings. Reference characters between 1 and 99 refer to overall features of the invention. Laminae are numbered 100, 200, 300, 400, 500, 600, 700, 800, 900, 1000, and 1100, and specific features on each respective lamina are numbered 101 to 199, 201 to 299, etc. with the last two digits corresponding to the overall feature of the invention. The suffix letter "V" is used to designate vias or interlamina vertical pathways through the structure. Suffixes comprising a hyphen and numeral (−1, −2, etc.) are used to designate parts of specific elements, such as individual branches of the branched manifolds. Numerals enclosed in curved braces { }designate crystal planes in a crystalline material.

Referring to FIG. 1, there is shown an apparatus 10 exemplary of the present invention. This apparatus 10 is comprised of a plurality of laminae, comprised of two groups, an outer group 12 and an inner group 14, fused together to form an integral structure. One or more inlet ports 20 and 24 enable the flow of reactants into the apparatus and one or more outlet ports 30 and 34 enable the flow of the resulting reaction products out of the apparatus. It is to be appreciated that the inlet ports 20 and 24 and outlet ports 30 and 34 do not necessarily have to be positioned through the outer groups. These elements could be designed to meet the integral structure at the side of a lamina, for example. The laminae of the outer group 12 and the inner group 14 may be comprised of either the same or different materials. The outer group 12, comprised of a first lamina 100 and an eleventh lamina 1100, may be comprised either of metal, ceramic or a glass material such as borosilicate glass or of materials from groups III, IV or V of the Periodic Table. For the specific chemical process example described below, borosilicate glass is the preferred material. The inner group 14 of the exemplary apparatus is comprised of laminae, also called wafers 200, 300, 400, 500, 600, 700, 800, 900, and 1000. The inner group preferably are comprised of materials selected to be compatible with the specific chemical process. For the specific chemical process example cited below the laminae of the inner group is preferably selected from groups III, IV or V of the Periodic Table, more preferably from group IV A, with silicon being the most preferred material. Section lines 4—4 and 5—5 depict the locations of sectional views of the two subsequent figures.

Figure 2:
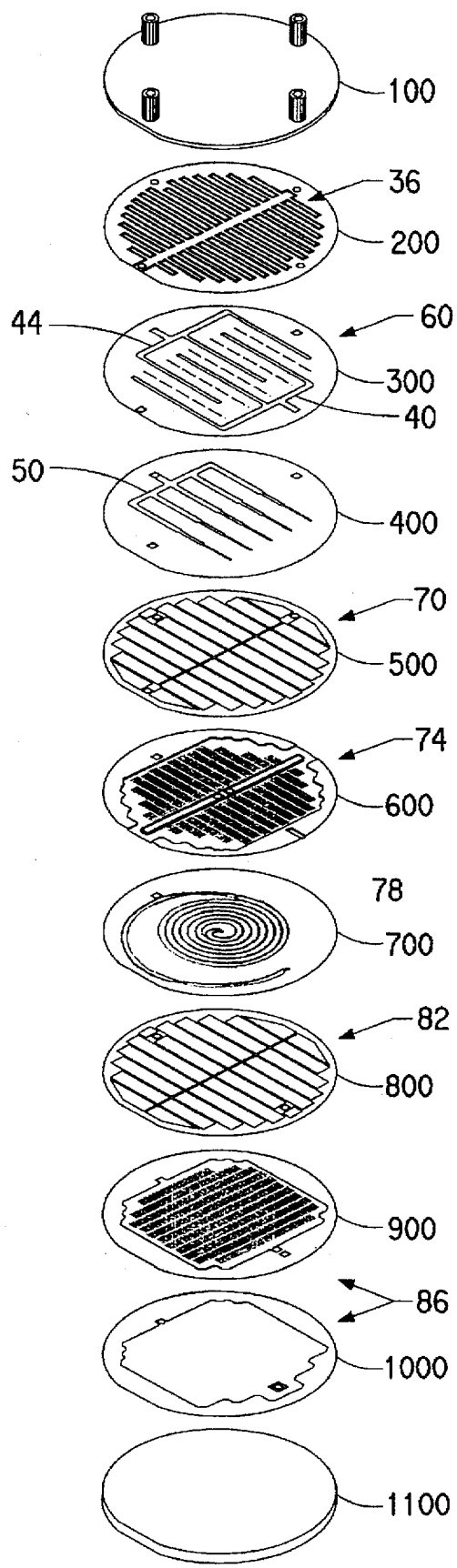
FIG. 2 is an exploded perspective view of the apparatus, as seen from above, showing the top surfaces of the laminae which are used to form the structure.
Figure 3:
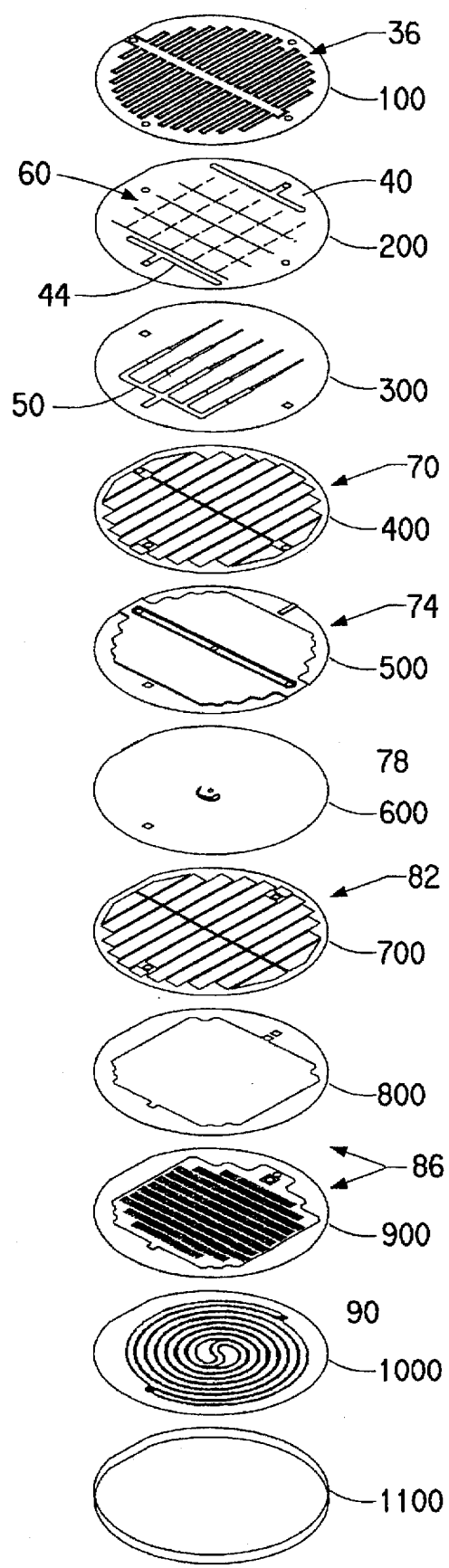
FIG. 3 is an exploded perspective view of the apparatus, as seen from below, showing the bottom surfaces of the laminae which are used to form the structure.

Illustrative operative features of the apparatus are shown in FIGS. 2 and 3 as follows: an electrical heater 36 formed by corresponding clearance pathways in the bottom of wafer 100 and metallization pattern on the top of wafer 200; two inlet distribution manifolds 40, 44 formed by pathways in the bottom of wafer 200 and the top of wafer 300; an array 60 of mixer/reaction chambers formed by corresponding pathways in the bottom of wafer 200 and the top of wafer 300; a fork-shaped outlet collection manifold 50 formed by corresponding pathways in the bottom of wafer 300 and the top of wafer 400; a first thermal barrier 70 formed by evacuated chambers 72 (FIG. 9) in the bottom of lamina 400 and the top of lamina 500; a first heat exchanger 74 formed by pathways in the bottom of wafer 500 and the top of wafer 600; a spiral separator 78 formed by pathways in the bottom of wafer 600 and the top of wafer 700; a second thermal barrier 82 formed by evacuated chambers 84 (FIG. 12) in the bottom of lamina 700 and the top of lamina 800; a second heat exchanger 86 formed by pathways in the bottom of wafer 800 and the top of wafer 900 and in the bottom of wafer 900 and the top of wafer 1000; and a spiral photoreactor chamber 90 formed by pathways in the bottom of wafer 1000 and the top surface of wafer 1100.

Figure 4:
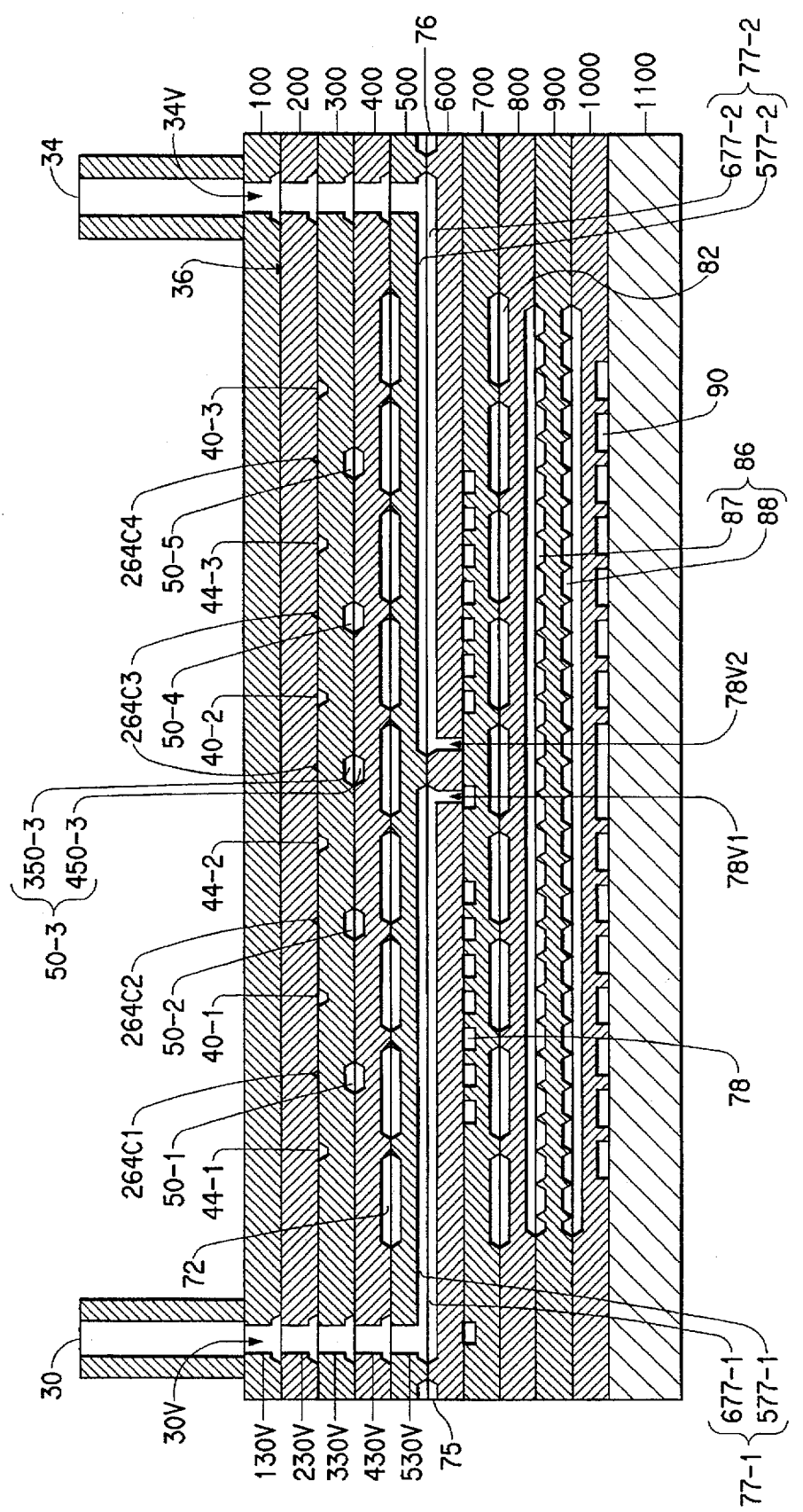
FIG. 4 is an enlarged first sectional view, taken along section lines 4—4 of FIG. 1.
Figure 5:
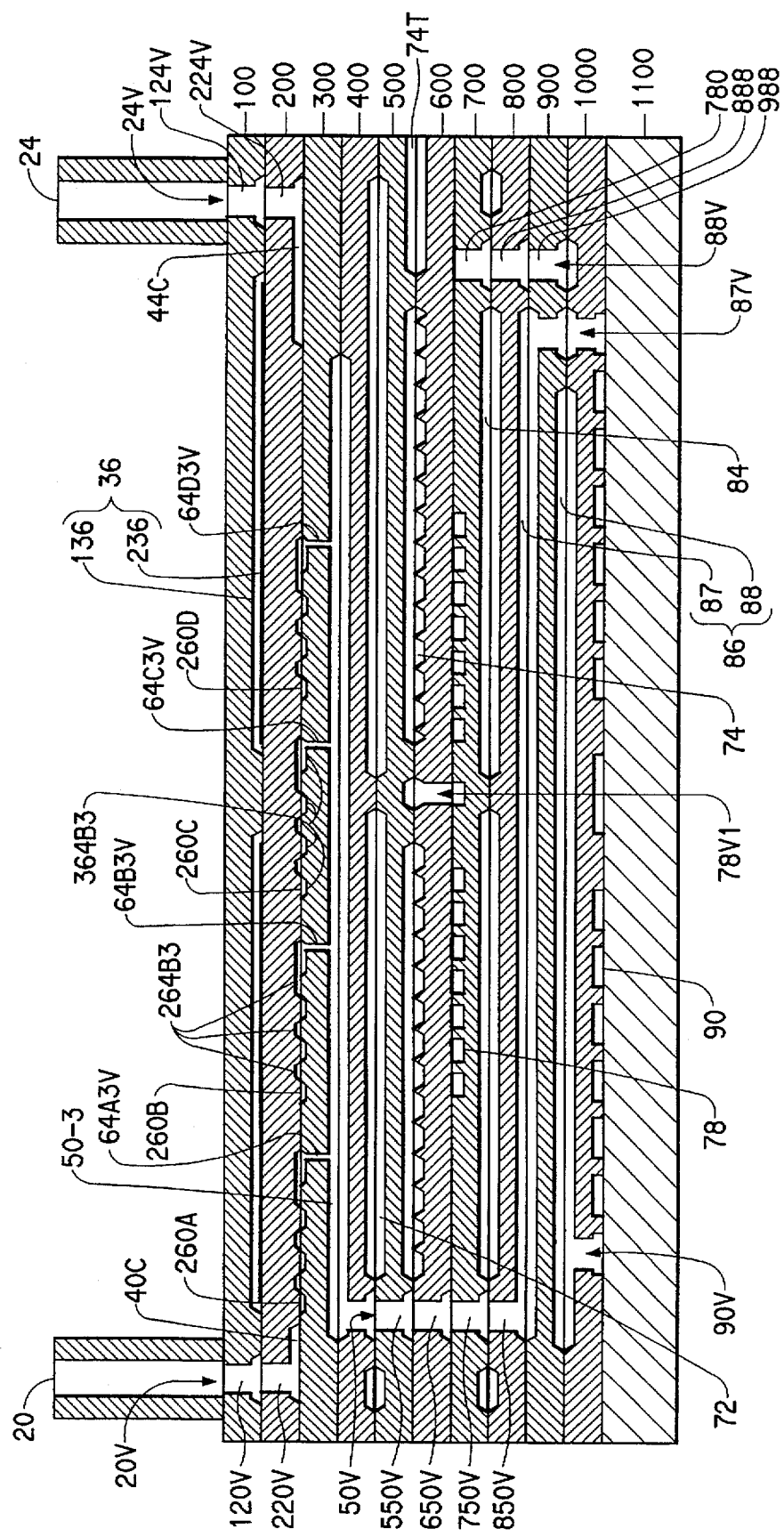
FIG. 5 is an enlarged second sectional view, taken along section lines 5—5 of FIG. 1.

In FIGS. 4 and 5 the vertical scale is exaggerated for clarity of illustration. Although the laminae of the apparatus are fused into an integral structure when completely fabricated, for clarity of illustration the interfaces between the laminae are shown in FIGS. 4 and 5.

In FIGS. 4 and 5, which illustrate typical flow passages in the interior of the structure, the vertical passages or vias 20V, 24V, 30V, 31V which connect respectively with the inlet ports 20, 24 and outlet ports 30, 34 in outer lamina 100, are typically formed by grinding or drilling through the top side of the wafer. The electrical heater 36 is formed by corresponding mirror image clearance pathways 136 (FIG. 6) in the bottom surface of lamina 100 and metallization pattern 236 (FIG. 6) on the top surface of lamina 200. The clearance pathways 136 in the exemplary apparatus are formed using an etching technique. The metallization pattern 236 on the top surface of lamina 200 is formed by standard tungsten chemical vapor deposition techniques using tungsten hexafluoride and hydrogen.

In FIG. 4 three passages 40-1, 40-2, 40-3, which are branches of distribution manifold 40 and three passages 44-1, 44-2, 44-3, which are branches of distribution manifold 44 are formed in the top surface of lamina 300. Five passages 50-1, 50-2, 50-3, 50-4, 50-5, which are branches of collection manifold 50, are respectively formed by corresponding mirror image pathways 350-1, 350-2, 350-3, 350-4, 350-5 (FIG. 8) in the bottom surface of lamina 300 and pathways 450-1, 450-2, 450-3, 450-4, 450-5 (FIG. 8) in the top surface of lamina 400.

In FIG. 5 the central axis of a third horizontal passage 50-3 (FIG. 8), which comprises the center branch of a 5-branch collection manifold 50, lies in the plane of the sectional view. The horizontal passage 50-3 is formed by corresponding mirror image pathways, respectively pathway 350-3 (FIG. 8) in the bottom surface of lamina 300 and pathway 450-3 (FIG. 8) in the top surface of lamina 400. The passages which comprise the 5-branch collection manifold 50 in the exemplary apparatus are formed using an etching technique.

In FIG. 5 passages 260A, 260B, 260C, 260D, in respective combination with the branches 40-1, 44-1, 40-2, 44-2, and 40-3, 44-3 of distribution manifolds 40, 44 (FIGS. 4 and 7) forms a group of T-mixer structures 62 whose operation will be subsequently described in conjunction with FIGS. 7 and 7A. The passages 264 in the bottom of the lamina 200 and the passages 364 in the top of lamina 300 cooperate to form a mixing chamber 64. The left side of FIG. 5 shows the vertical passage 20V, which extends through lamina 100, 200 to connect inlet port 20 with the common chamber 40C of manifold 40, is formed by correspondingly positioned pathways 120V, 220V in laminae 100, 200.

The right side of FIG. 5 shows vertical passage 24V, which extends through lamina 100, 200 to connect inlet port 24 with common chamber 44C of manifold 44, is formed by correspondingly positioned pathways 124V, 224V in laminae 100, 200. A center horizontal passage 50-3 of 5-branch manifold 50 is formed by corresponding mirror image pathways 350-3 and 450-3 (FIG. 8) in the bottom surface of lamina 300 and the top surface of lamina 400, respectively.

The left side of FIG. 5 shows the vertical passage 50V, which extends through laminae 400, 500, 600, 700, 800 to connect second heat exchanger 86 with manifold 50. Vertical passage 50V is formed by correspondingly positioned pathways 450V, 550V, 650V and 750V, 850V respectively in laminae 400, 500, 600, 700, and 800.

Figure 6:
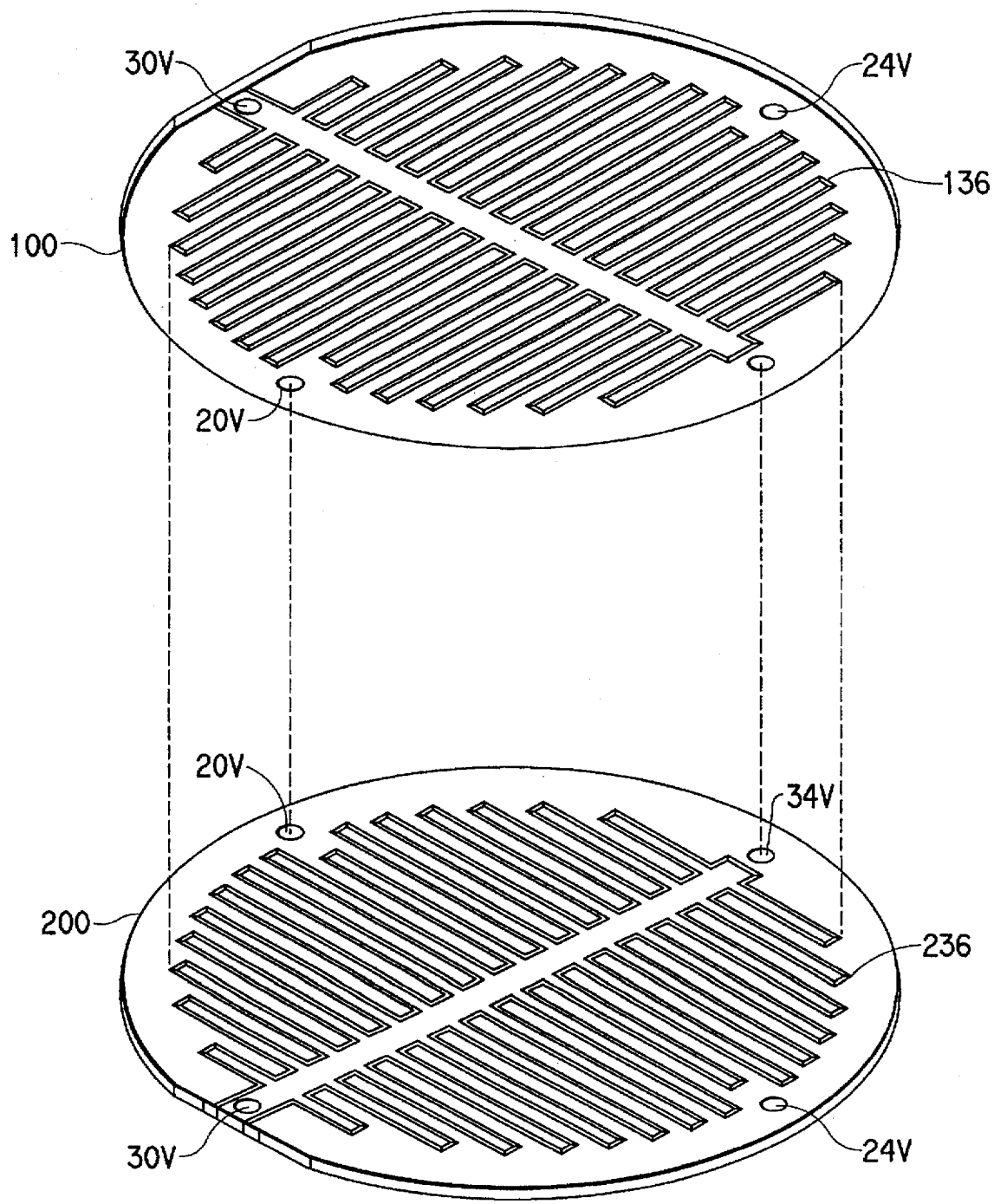
FIG. 6 is an exploded perspective view of a portion of the apparatus showing the bottom surface of a first lamina and the top surface of the second lamina showing a typical arrangement of clearance channels and a metallization pattern that forms an electrical heater.

FIG. 6 shows a typical arrangement of clearance channels and metallization pattern that cooperate to form an electrical heater. The electrical heater 36 shown is comprised of a metallized pattern 236 deposited on the top surface of lamina 200 and a clearance pathway 136 in the bottom surface of lamina 100. When assembled, the clearance pathway permits the planar surfaces of the two laminae to be bonded together. Alternate arrangements, such as forming the metallized pattern in an etched pathway in either the bottom surface of lamina 100 or the top surface of lamina 200, with the top of the metallized pattern flush with the surface of the lamina, could be employed.

Figure 7:
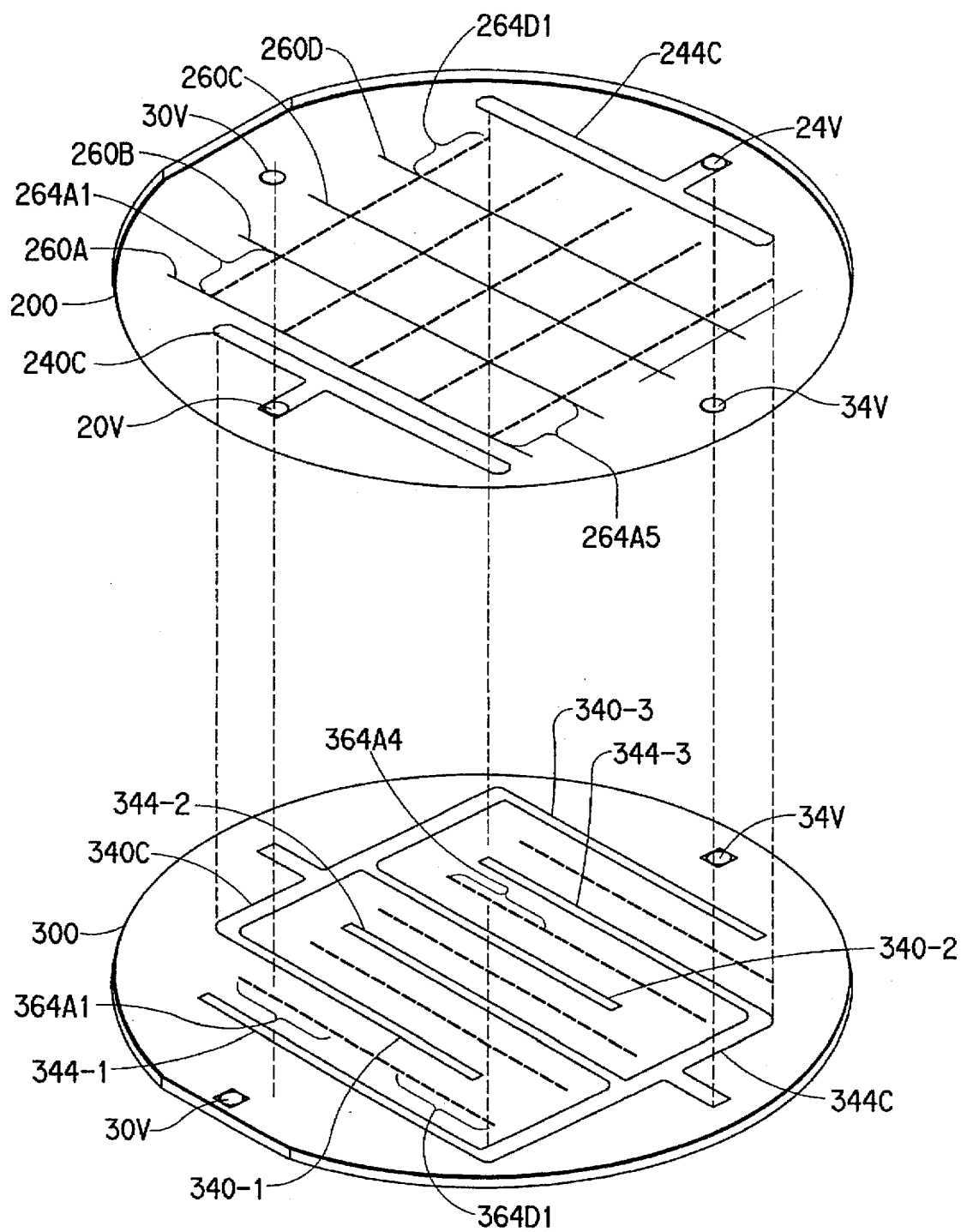
FIG. 7 is an exploded perspective view of the bottom of a second lamina of the apparatus and the top of a third lamina of the apparatus showing the arrangement of pathways that form an array of mixing elements and a distribution manifold.
Figure 7A:
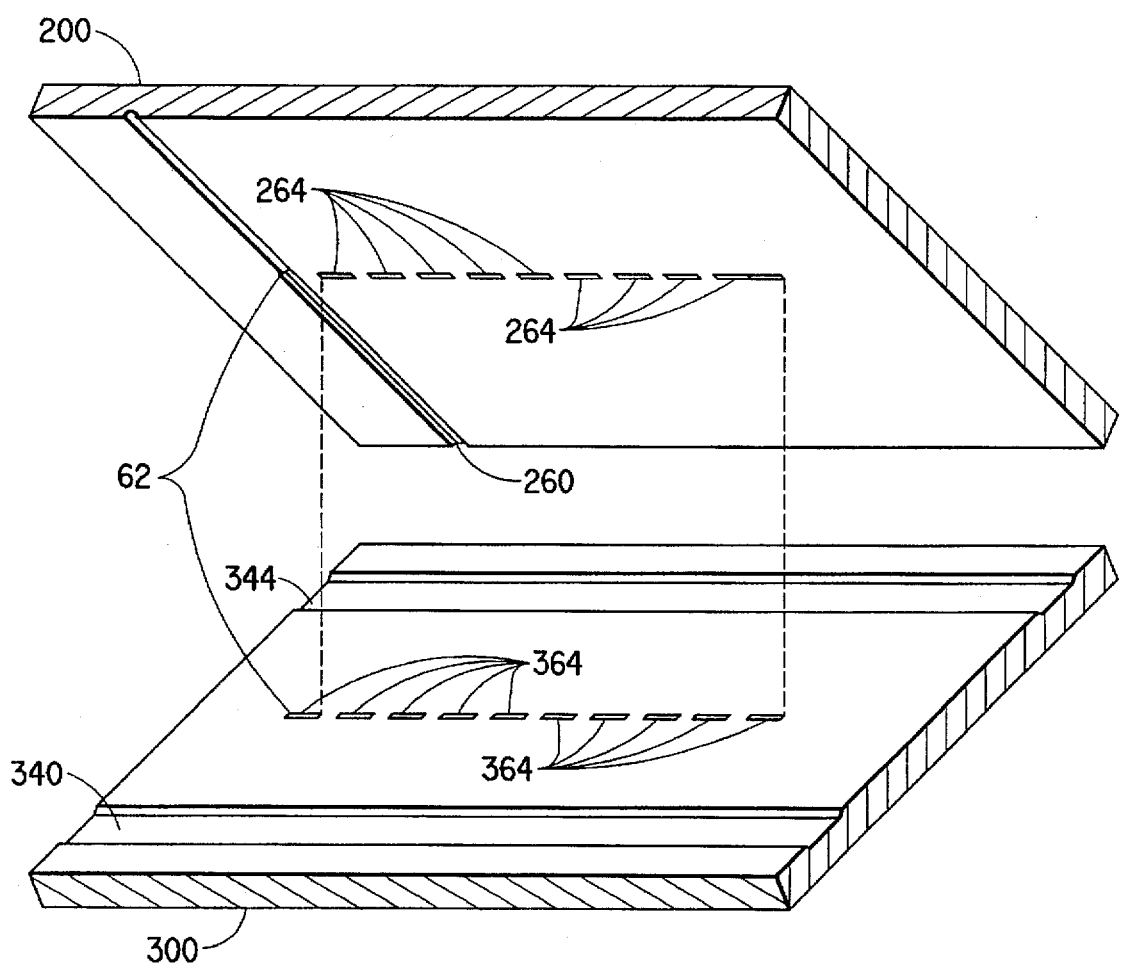
FIG. 7A is an enlarged perspective view of a portion of FIG. 7 showing the arrangement of pathways that form the combination of a single T-mixer and single serpentine mixing element.

FIG. 7 shows an arrangement of pathways that cooperate to form an array of mixer chambers and a distribution manifold. First distribution manifold 40 is comprised of common chamber 40C and branch passages 40-1, 40-2, 40-3. Chamber 240C, on the bottom surface of the second lamina 200, in combination with the chamber 340C on the top of wafer 300 form the chamber 40C. Pathways 340-1, 340-2, 340-3 on the top of wafer 300, form branch 40-1, branch 40-2, and branch 40-3 respectively, of distribution manifold 40. Also shown is the opening of vertical pathway 20V which connects input port 20 with the common chamber 40C.

Second distribution manifold 44 is comprised of common chamber 44C and branch passages 44-1, 44-2, 44-3. Chamber 244C, on the bottom surface of the second lamina 200, in combination with the chamber 344C on the top of wafer 300 form the chamber 44C. Pathways 344-1, 344-2, 344-3 on the top of wafer 300, form branch 44-1, branch 44-2, and branch 44-3, respectively, of distribution manifold 44. Also shown is the opening of vertical pathway 24V which connects input port 24 with the common chamber 44C.

A series of segmented pathways 264 are formed on the bottom surface of the second lamina 200, which cooperate with corresponding segmented pathways 364 of lamina 300, to form the series of mixing elements 64 of the mixer array 60. The mixer array 60 comprises multiple groups 60A, 60B, 60C, 60D of multiple parallel mixers 64. In the specific example shown, there are five mixers in each group, that are respectively designated 64A-1, 64A-2, 64A-3, 64A-4, 64A-5 through 64D-1, 64D-2, 64D-3, 64D-4, 64D-5. FIG. 7 shows chambers 240C and 244C, previously mentioned.

Each mixer 64 is comprised of two pathways, a first pathway 264 formed on the bottom of the second lamina 200 and a second pathway 364 formed on the top of the third lamina 300. The first and second pathways are each comprised of a series of straight segments, alternating with each other, connected together to form a continuous path. The first and second pathways are positioned on abutting surfaces with the segments longitudinally offset such that the segments intersect. The overall mixer 64 may be described as having a serpentine path (best seen in FIG. 5).

Four pathways 260A, 260B, 260C and 260D, cooperate respectively with branches 40-1, 40-2, 40-3 of manifold 40, branches 44-1, 44-2, 44-3 of manifold 44 and a first segment of each segmented pathway 364 to form a series of T-mixers 62. Each first segment 364 thus connects each T-mixer 62 with each serpentine mixer 64 of mixer array 60. As best seen in FIG. 7A, each pathway 260 cooperates with manifolds 40 and 44 and a first segment of each segmented pathway 364 to form a T-mixer 62, which connects with a serpentine mixer 64, comprised of the multiple segments 264 and 364. As also may be seen in FIG. 7A each portion of pathway 260, between manifold 40 and segment 364 and between manifold 40 and segment 44, may be of a different cross-sectional size to provide the desired flow rate of each chemical being mixed. The number of segments 264 and 364 and the cross-sectional size of each segment 264 and 364 may be selected, according to the mixing requirements and flow characteristics of the chemicals being processed.

Figure 8:
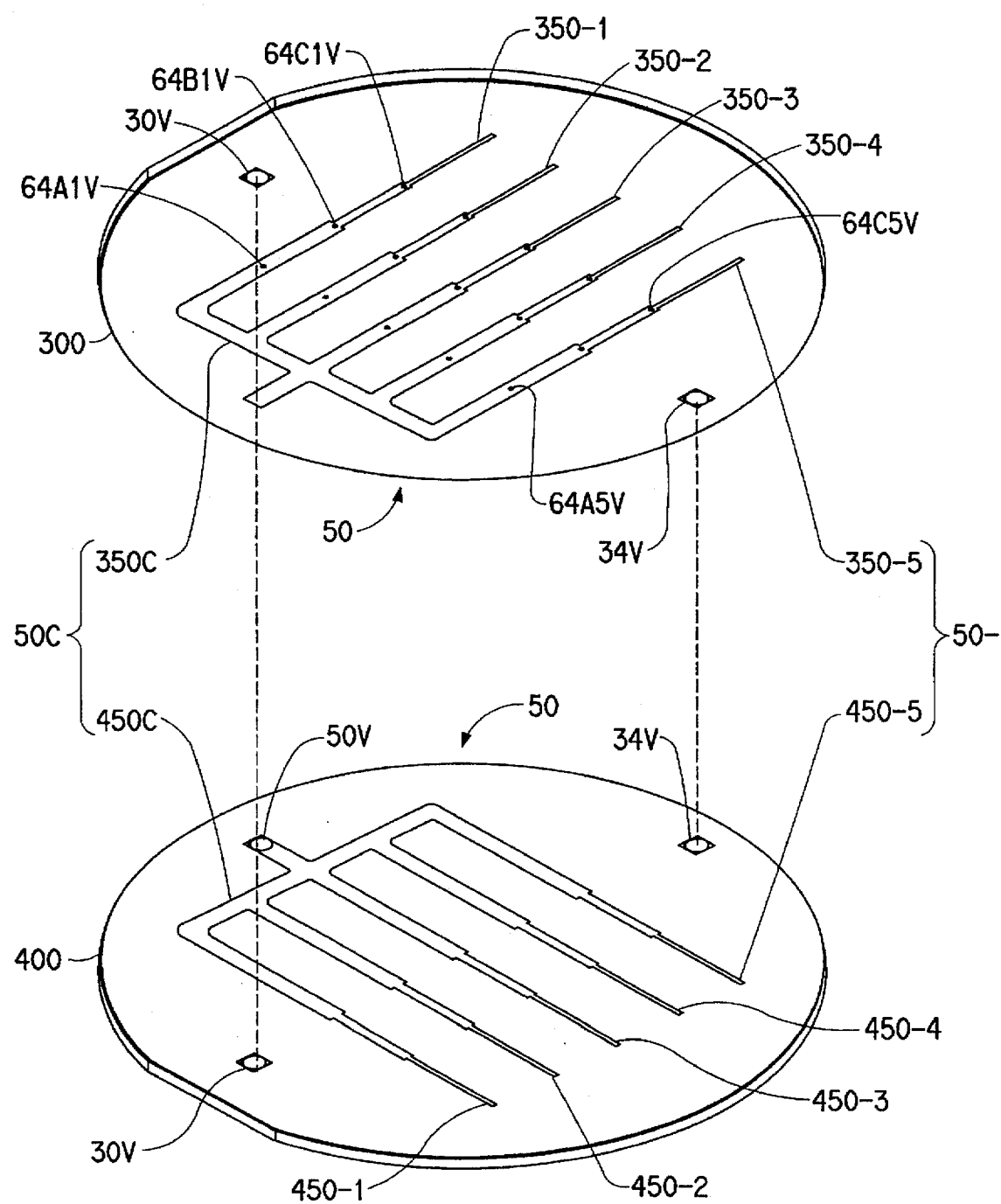
FIG. 8 is an exploded perspective view of the bottom of a third lamina of the apparatus and the top of a fourth lamina of the apparatus showing the arrangement of pathways that form a collection manifold.

FIG. 8 shows the arrangement of pathways that cooperate to form a collection manifold 50, which is branched and has a varying cross-sectional size. Distribution manifold 50 is comprised of common chamber 50C and branch passages 50-1, 50-2, 50-3, 50-4, and 50-5. The vertical pathways 64A-1V, 64A-2V, 64A-3V, 64A-4V, and 64A-5V connects passages 264A with the collection manifold branches 50-1, 50-2 50-3, 50-4, and 50-5, respectively; the vertical pathway 64B-1V, 64B-2V, 64B-3V, 64B-4V, and 64B-5V connects passages 264B with the collection manifold branches 50-1, 50-2, 50-3, 50-4, and 50-5, respectively; the vertical pathway 64C-1V, 64C-2V, 64C-3V, 64C-4V, and 64C-5V connects passages 264C with the collection manifold branches 50-1, 50-2, 50-3, 50-4, and 50-5, respectively; and the vertical pathway 64D-1V, 64D-2V, 64D-3V, 64D-4V, and 64D-5V connects passages 264D with the collection manifold branches 50-1, 50-2, 50-3, 50-4, and 50-5, respectively. Vertical passage 50V connects collection manifold 50 with the photoreactor 90, to be described below in conjunction with FIG. 15.

Figure 9:
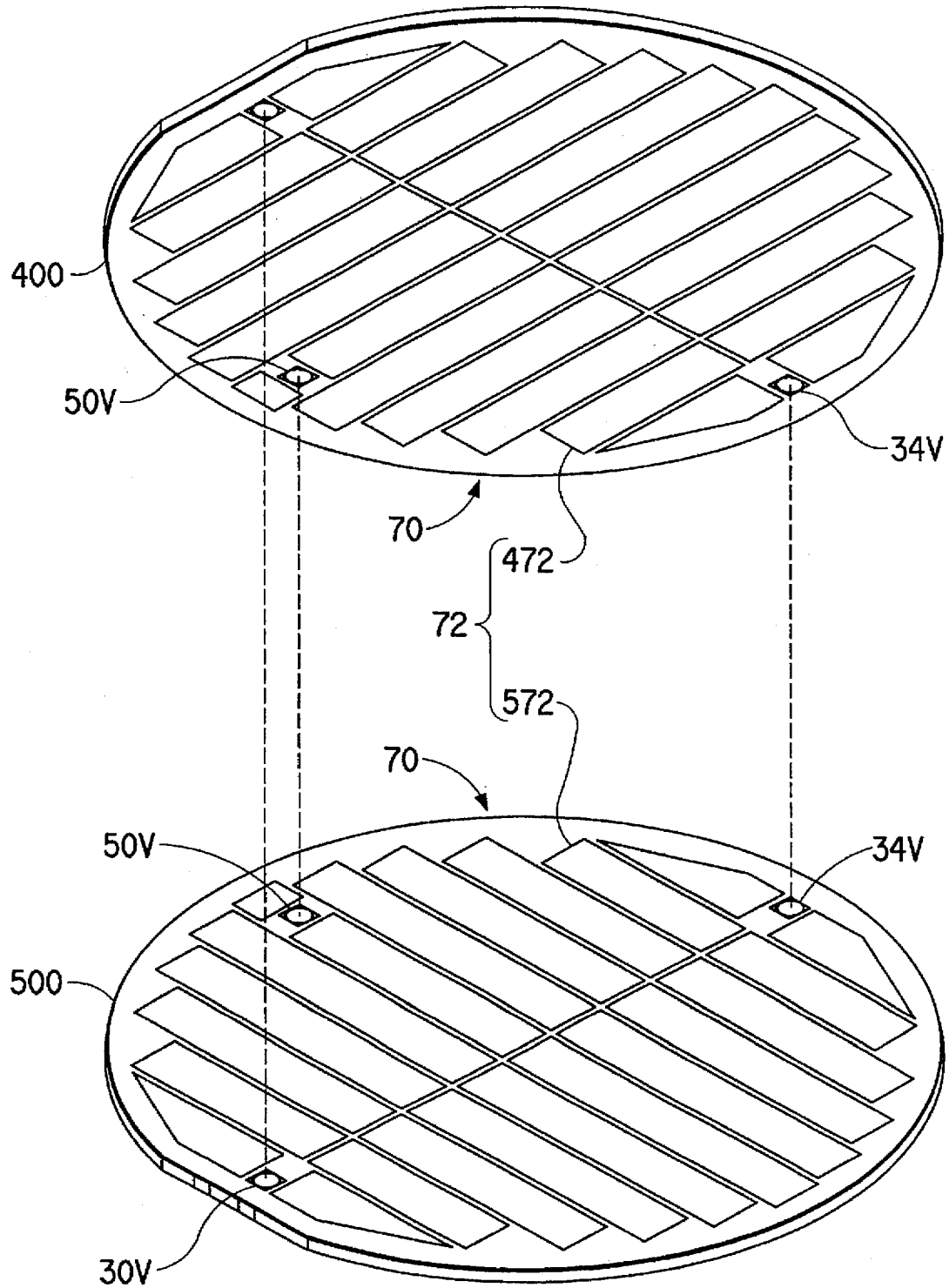
FIG. 9 is an exploded perspective view of the bottom of a fourth lamina and the top of a fifth lamina of the apparatus showing the arrangement of pathways that form a first thermal barrier.

FIG. 9 shows the arrangement of chambers 72 that cooperate to form a first thermal barrier 70. Chambers 472, etched into the bottom of wafer 400 are aligned with chambers 572, etched into the top of wafer 500 cooperate to form chambers 72. During the bonding process the wafers are placed in a vacuum chamber, so that a vacuum is present in each of chambers 72. Since a vacuum does not readily conduct heat, and since there is very little contact area between the bottom of wafer 400 and the top of wafer 500, a thermal barrier is created that greatly reduces the flow of heat vertically within the chemical processing unit. This effectively thermally isolates the combination of the electrical heater 36 and the mixer array 60 from the remainder of the chemical processing unit.

Figure 10:
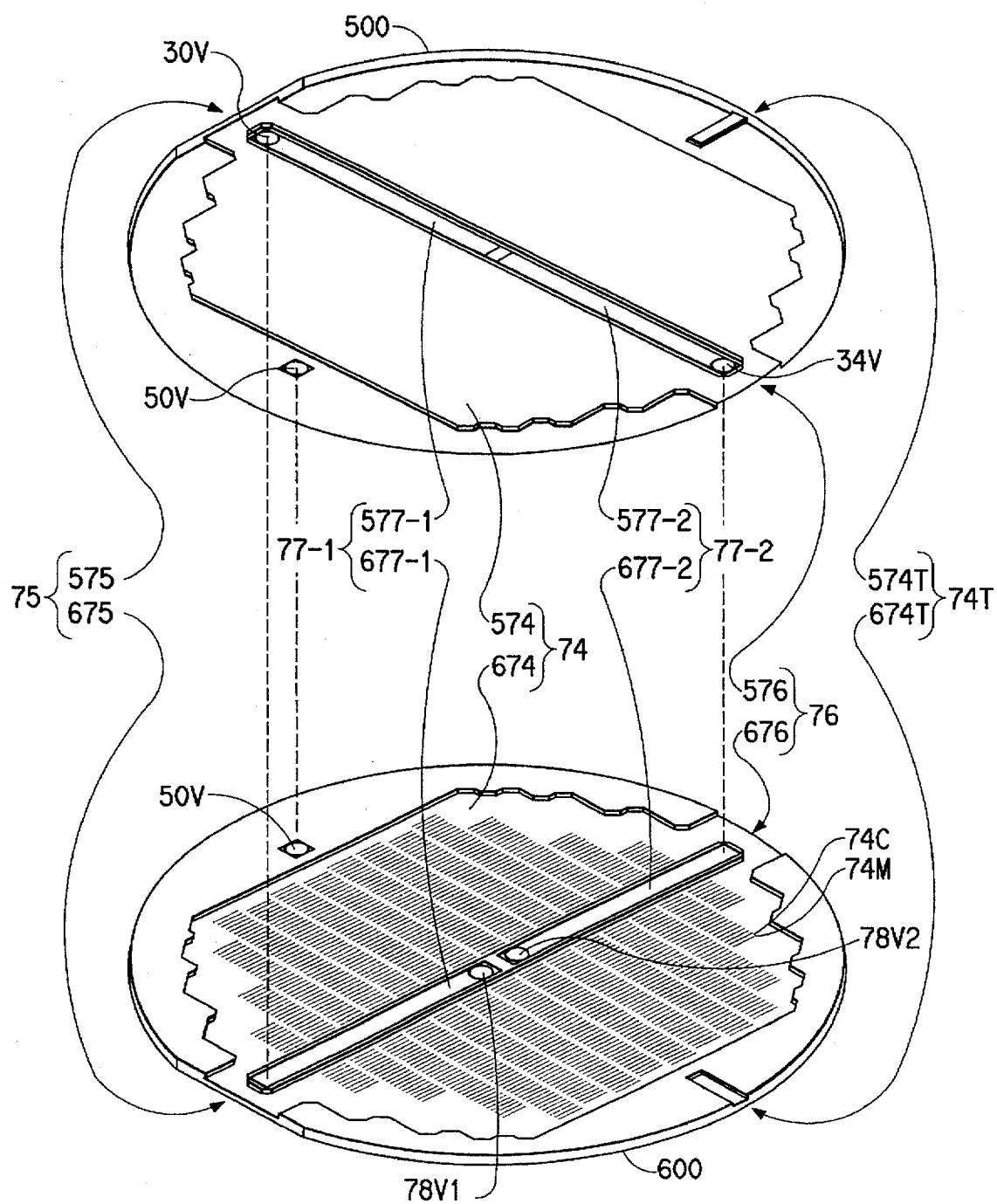
FIG. 10 is an exploded perspective view of the bottom of a fifth lamina and the top of a sixth lamina of the apparatus showing the arrangement of pathways that form a first heat exchanger assembly.

FIG. 10 shows the arrangement of pathways that form a first heat exchanger assembly 74. A heat exchanger chamber 574 is formed in the bottom surface of wafer 500. A series of channels 74C and mesas 74M are formed in the top surface of wafer 600 to increase the effective surface area to enhance heat transfer. An inlet port 75 (FIG. 1) is formed by corresponding pathways 575 and 675 and outlet port 76 is formed by corresponding pathways 576 and 676. A thermocouple well 74T, formed by corresponding pathways 574T and 674T is provided to facilitate monitoring the temperature of the heat exchanger. External flow control means (not shown) may be used for controlling the temperature of the heat exchanger. In operation, a flow of heat exchanging fluid enters through inlet port 75, passes through channels 74C and around mesas 74M and exits through outlet port 76. Two passages 77-1 and 77-2 connect vertical passages 78V-1 and 78V-2, described below, with vertical passages 30V and 34V respectively.

Figure 11:
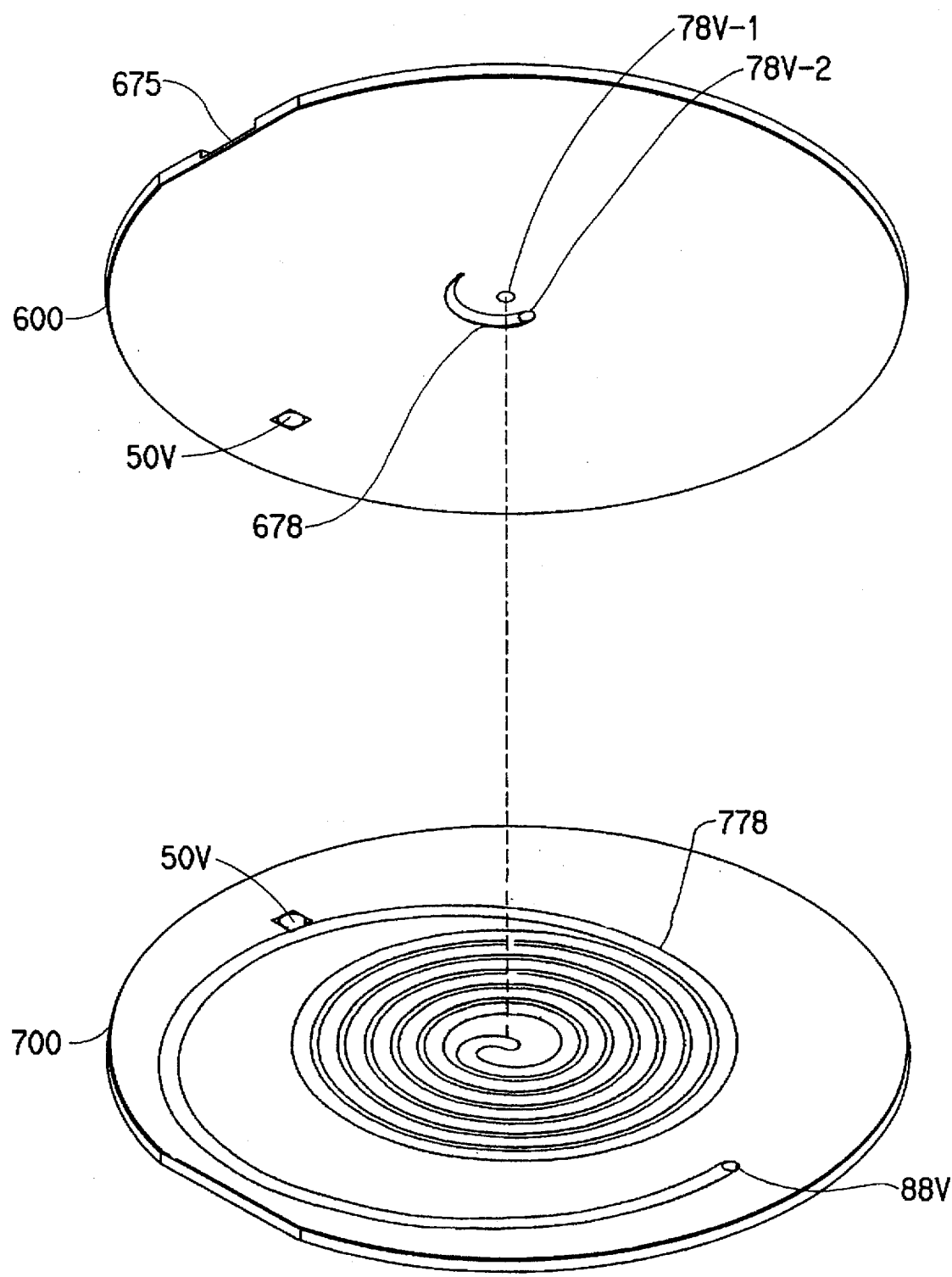
FIG. 11 is an exploded perspective view of the bottom of a sixth lamina and the top of a seventh lamina, showing the arrangement of pathways that form a spiral separator assembly.

FIG. 11 shows an arrangement of pathways in the bottom of wafer 600 and the top of wafer 700 that cooperate to form a spiral separator assembly 78. The short exit path 678 is etched in the bottom surface of wafer 600 and the long spiral path 778 is etched in the top surface of wafer 700 using an isotropic etching technique. Vertical passage 88V extends through wafer 700 and connects the output of the second heat exchanger with the inlet of the spiral separator 78. Vertical passages 78V-1 and 78V-2 extend through wafer 600 to connect the outputs of the separator to the passages 77-1 and 77-2, respectively (FIG. 10).

Figure 12:
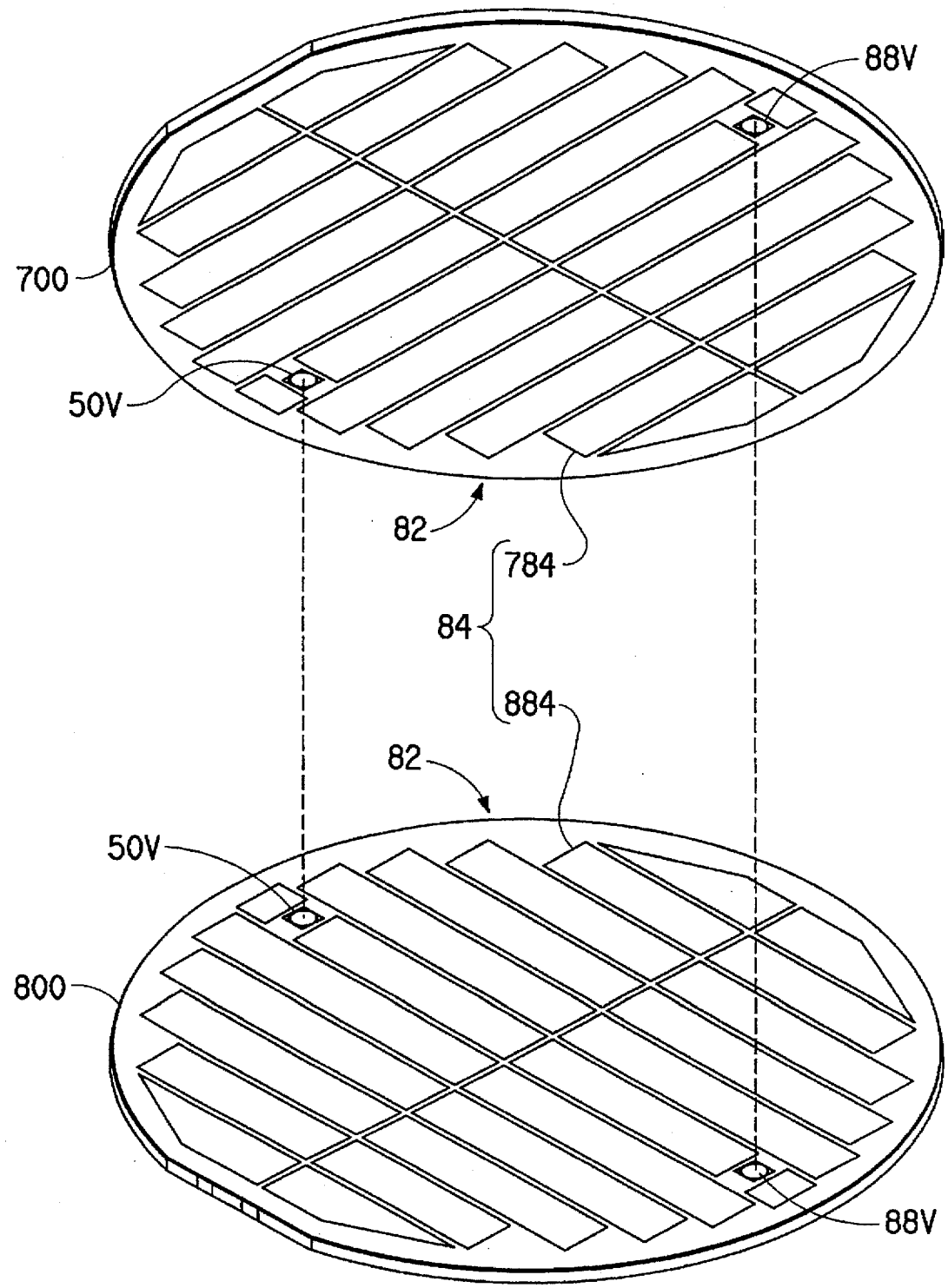
FIG. 12 is an exploded perspective view of the bottom of a seventh lamina and the top of an eighth lamina of the apparatus showing the arrangement of pathways that form a second thermal barrier.

FIG. 12, in a manner similar to that described in conjunction with FIG. 9, shows the arrangement of chambers 84 that form a second thermal barrier 82. Chambers 784, etched into the bottom of wafer 700 are aligned with chambers 884, etched into the top of wafer 800 cooperate to form chambers 84. During the bonding process the wafers are placed in a vacuum chamber, so that a vacuum is present in each of chambers 84. Since a vacuum does not readily conduct heat, and since there is very little contact area between the bottom of wafer 700 and the top of wafer 800, a thermal barrier is created that greatly reduces the flow of heat vertically within the chemical processing unit. This effectively thermally isolates the combination of the first heat exchanger 74 and spiral separator 78 from the remainder of the chemical processing unit.

Figure 13:
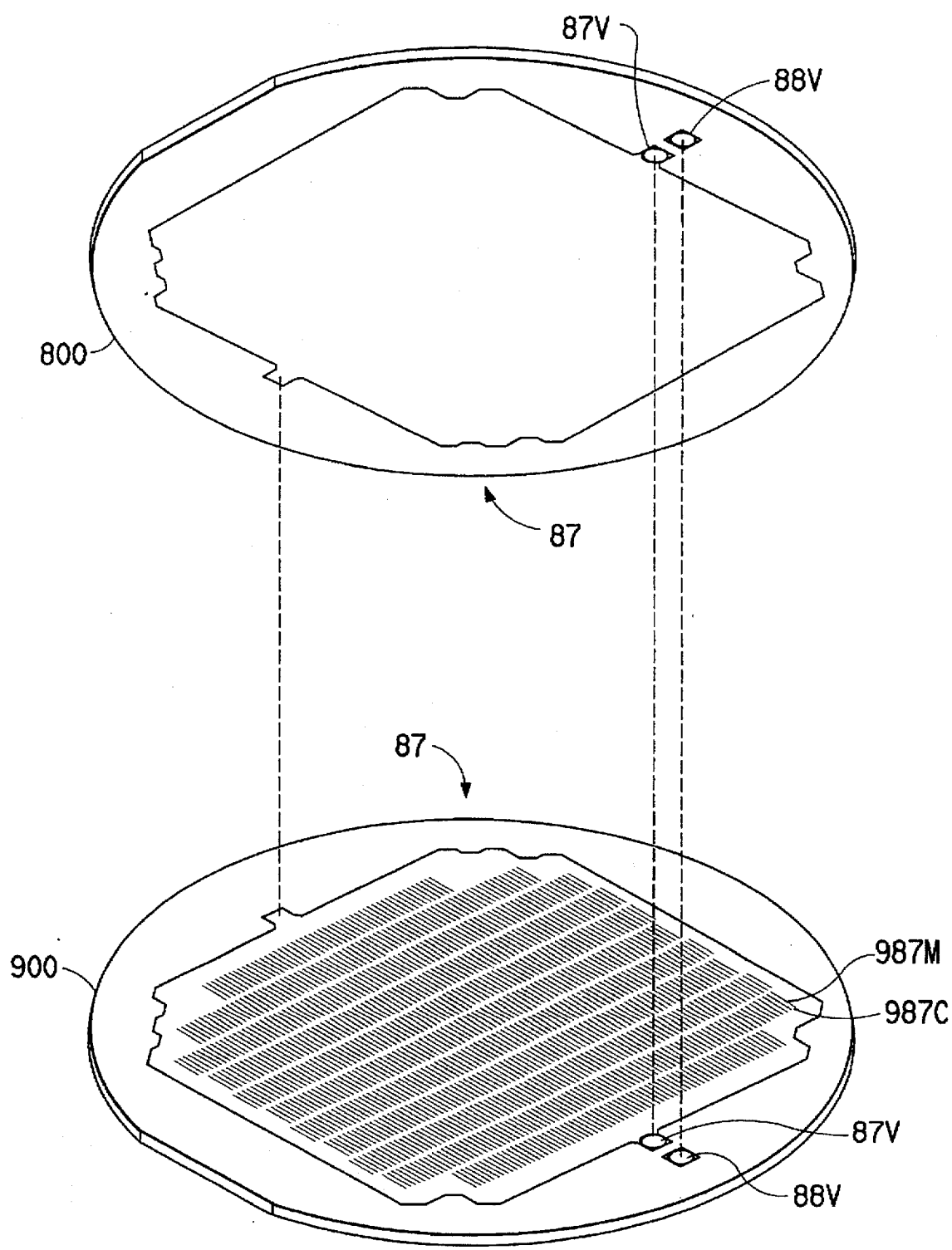
FIG. 13 is an exploded perspective view of the bottom of an eighth lamina and the top of a ninth lamina of the apparatus showing the arrangement of pathways that form a first part of a second heat exchanger assembly.
Figure 14:
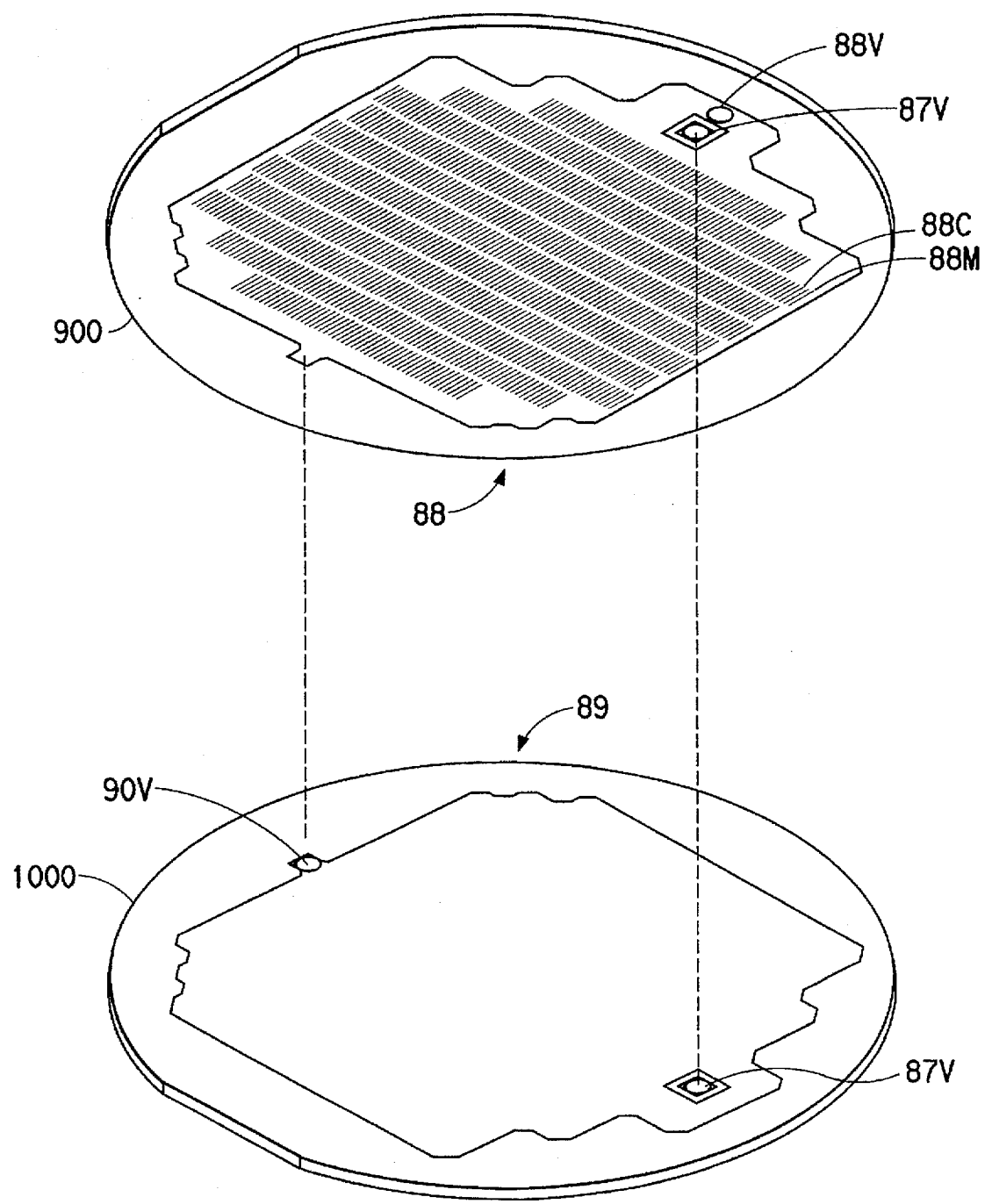
FIG. 14 is an exploded perspective view of the bottom of a ninth lamina and the top of a tenth lamina, showing the arrangement of pathways that form a second part of a second heat exchanger assembly.

FIGS. 13 and 14 show the arrangement of pathways that form a second heat exchanger assembly 86 (FIGS. 2 and 3). Heat exchanger 86 comprises both the passages 87 of FIG. 13, through which the mixed, but yet unreacted, reactants flow and the passages 88 of FIG. 14 through which the chemically reacted material flows. This heat exchanger transfers heat between the chemically reacted material flowing from the photoreactor and the mixed reactants flowing into the heat exchanger from the mixer array 60 (FIG. 7) through vertical passage 50V. As may be seen in FIG. 13, a series of channels 87C (formed by 987C) and mesas 87M (formed by 987M) are featured in the top surface of wafer 900 to increase the effective surface area to enhance heat transfer.

As may be seen in FIG. 14 a series of channels 88C and mesas 88M are formed in the bottom surface of wafer 900 and a chamber 89 is formed in the top surface of wafer 1000. The channels 88C and mesas 88M in the bottom of wafer 900 and the channels 87C and mesas 87M (FIG. 13) in the top of wafer 900 serve to increase the effective surface area to enhance heat transfer through wafer 900. In operation the reacted material flows from the photoreactor 90 through vertical passage 90V and into passages 88. This material then flows through channels 88C and around and over mesas 88M and into vertical passage 88V.

Figure 15:
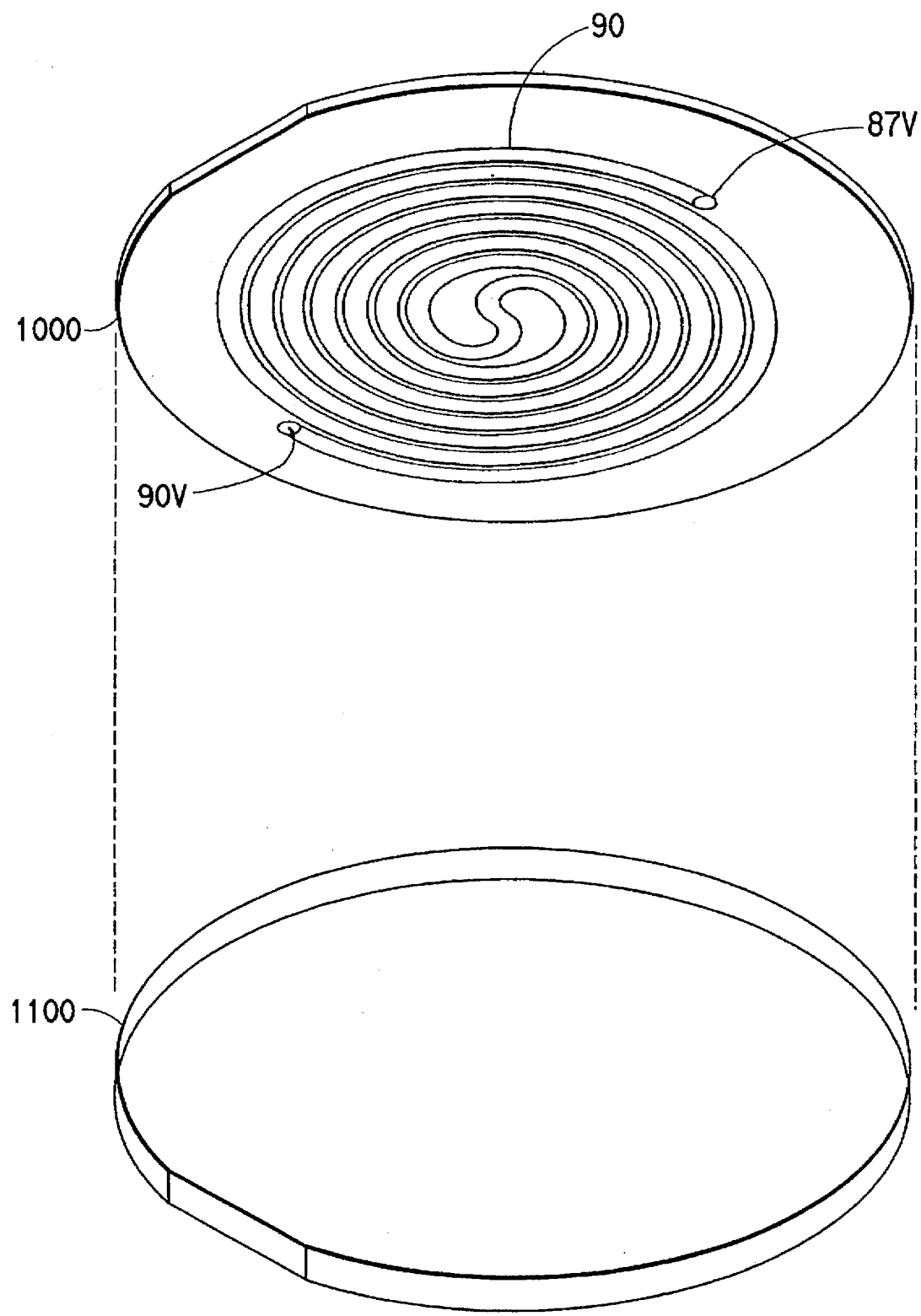
FIG. 15 is an exploded perspective view of the bottom of a tenth lamina and the top of an eleventh lamina, showing the arrangement of pathways that form a spiral path photo-reactor assembly.

FIG. 15 shows the arrangement of a folded spiral pathway that forms a photoreactor 90. In operation the mixed material enters the spiral through vertical passage 87V, flows spirally toward the center of the wafer in a counterclockwise direction, reverses direction and flows spirally outwardly in a clockwise direction and exits through vertical passage 90V. An external source, typically ultraviolet, of actinic radiation 99 (FIG. 1) passes through the transparent outer lamina 1100 to irradiate the material in the spiral photoreactor 90 to stimulate the desired chemical reaction.

Figure 16:
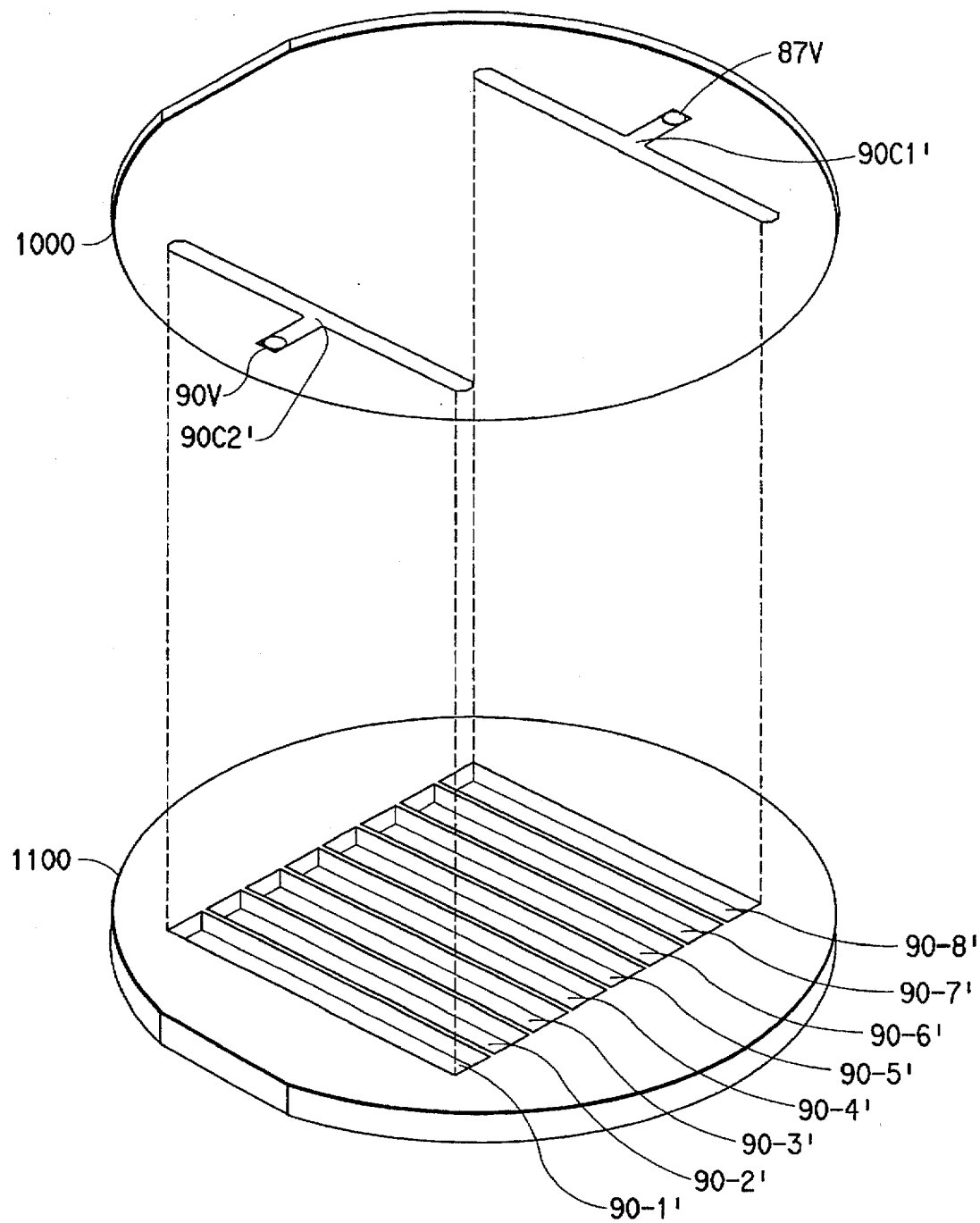
FIG. 16 is an exploded perspective view of a first alternate arrangement of the bottom of a tenth lamina and the top of an eleventh lamina, showing an arrangement of pathways that form a catalytic reaction chamber.

FIG. 16 shows a first alternate arrangement of a catalytic reactor 90', which may be used in place of the photoreactor 90. Reactor channels 90-1', 90-2', 90-3', 90-4', 90-5', 90-6', 90-7', and 90-8' may be packed with catalyst beads (not shown), or one or more layers of catalytic material may be deposited on the surfaces of these channels. In operation, the mixed material enters the catalytic reactor 90' through vertical passage 87V, flows into chamber 90C1' and is distributed into reactor channels 90-1' through 90-8'. The reacted material flows into chamber 90C2' and exits through vertical passage 90V.

Figure 17:
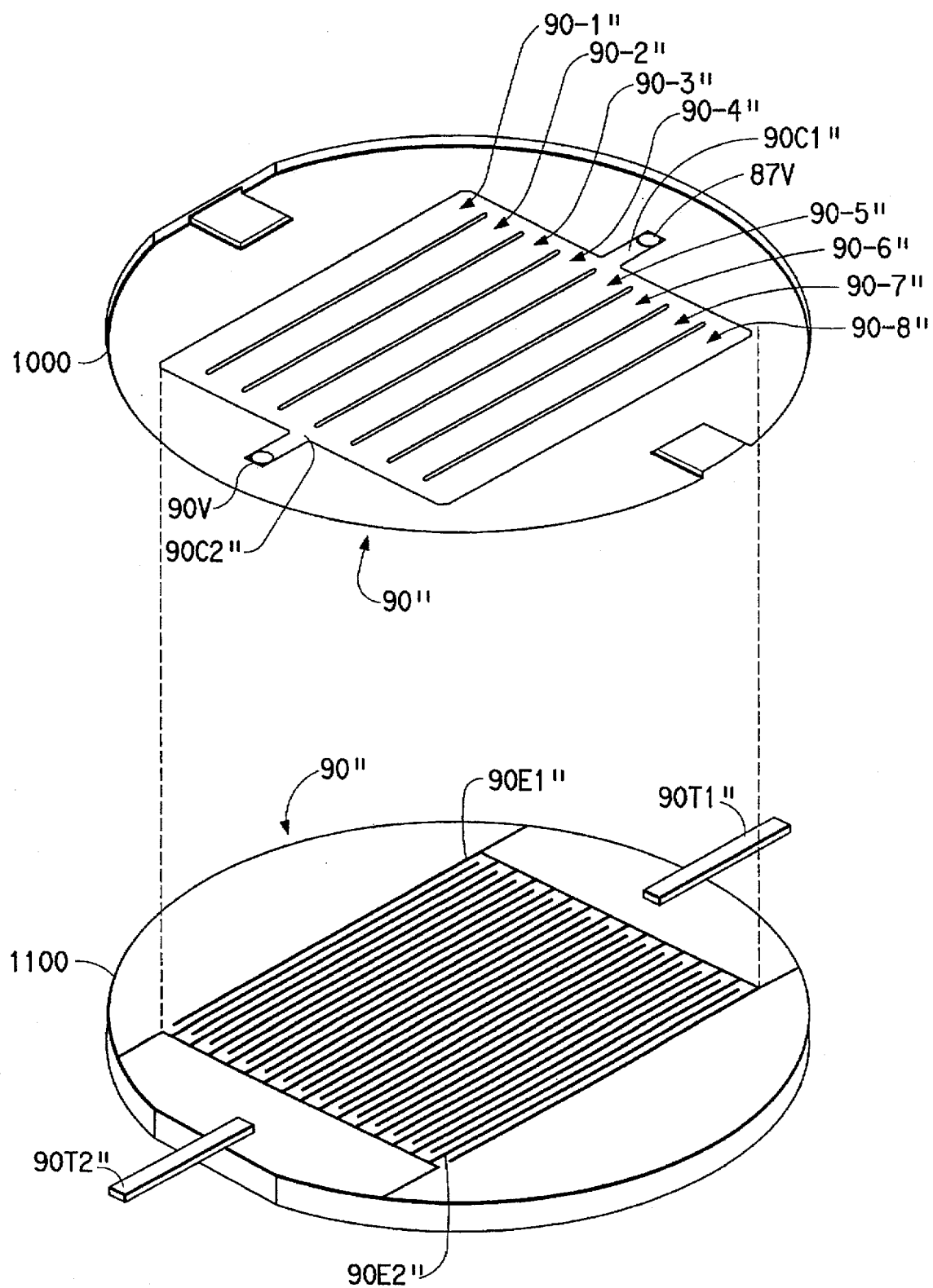
FIG. 17 is an exploded perspective view of a second alternate arrangement of the bottom of a tenth lamina and the top of an eleventh lamina, showing an arrangement of pathways that form an electrochemical reaction chamber.

FIG. 17 shows shows a second alternate arrangement of an electrochemical reactor 90", which may be used in place of either the photoreactor 90 or the catalytic reactor 90'. In operation, the mixed material enters the electrochemical reactor through vertical passage 87V, flows into chamber 90" and is distributed into reactor channels 90-1", 90-2", 90-3", 90-4", 90-5", 90-6", 90-7", and 90-8". Electrodes, such as the two interdigitated electrodes 90E1" and 90E2" shown, are connected, by terminals 90T1" and 90T2" to an external electrical source (not shown) to cause an electrical current to flow through the mixed materials and facilitate a chemical reaction. The reacted material flows into chamber 90C2' and exits through vertical passage 90V. As is known to those skilled in the electrochemical art the electrochemical reactor may optionally be shaped in alternate manners.

Multiple units of the integral chemical processing apparatus can be used in sequence or in tandem. Each multiple scheme affords advantages in throughput among other benefits. Sequential use would be, for example, where one unit performs mixing, and the mixed material is passed to the next unit which performs heating, and so on. Tandem use would be, for example, where all units perform the same function as an array. These concepts could even be integrated, as for example, where several units in tandem perform an operation with all output from the tandem units being fed into another (perhaps larger) unit in sequential fashion. The incorporation of units in any number of sequential or tandem patterns is a design choice to be made by those skilled in the art and according to the desired chemical processing result.

OPERATION OF THE INTEGRATED CHEMICAL PROCESSING APPARATUS

The two materials to be reacted flow into the unit through input ports 20, 24, through vertical passages 20V, 24V into distribution manifolds 40, 44 and into mixer array 60. Heater 36 preheats the mixer array 60 to the desired temperature. The mixed material is collected in collection manifold 50 and passed through vertical passage 50V to the second heat exchanger 86. After being adjusted to the desired temperature by heat exchanged with the reacted material, the mixed material passes through vertical passage 87V to the photoreactor 90. Actinic radiation from an external source 99 stimulates the desired reaction. The reacted material passes from the photoreactor through vertical passage 90V to the second heat exchanger 86. After exchanging heat with the incoming mixed material, the reacted material passes through vertical passage 88V to the spiral separator 78. The centrifugal force acting on the reacted material causes the denser portion to move to the outside of the spiral and to enter spiral 678 and proceed to vertical passage 78V-2. The less dense portion passes into vertical passage 78V-1. The first heat exchanger 74 maintains the spiral separator at the desired temperature. A separate heat exchanging fluid entering at inlet port 75 and exiting at outlet port 76 is used to control the temperature of the spiral separator 78. Material flowing through 78V-1 passes through passage 77-1 and then to outlet port 30 via vertical passage 30V. Material flowing through 78V-2 passes through passage 77-2 and then to outlet port 34 via vertical passage 34V.

Additional microfabricated process control elements, such as proportional valves, pressure, temperature and flow sensors, may be incorporated into the structure of the present invention. These elements, when used with external controls could regulate the flow in heat exchangers or residence time of reactants within the integrated chemical processing unit. Other chemical processes, such as hydrolysis, nitration, polymerization, and oxidation may be practiced using the integrated structure of the present invention.

METHOD OF FABRICATION

Most steps of the fabrication process for the apparatus of the exemplary chemical process generally correspond to known semiconductor processing techniques for silicon wafers. The photo-tools for the patterns for each side of each wafer are prepared using well known computer-aided-design techniques. Already polished silicon wafers, having the {100} crystal plane and other orientations on the major surfaces may be purchased from commercial sources. The polished wafers are first cleaned using a well-known general cleaning technique, such as the "RCA process". An oxide film is grown on the wafer using well-known standard techniques. A nitride layer is deposited over the oxide layer using a known chemical vapor deposition method. The nitride layer protects the oxide layer from attack by the etchant used to etch the silicon. A photoresist is applied, following the directions of the photo resist manufacturer, using the well-known spin coating technique.

The desired pattern is formed by first masking the wafer with a photo-tool having an image of the desired pattern, which is precisely aligned with the crystal planes of the wafer. Straight portions of the pattern are typically aligned along the {110} crystal plane. After exposing and developing the photoresist, the undeveloped photoresist is stripped to expose part of the nitride/oxide film layer. The exposed nitride/oxide film is finally etched to form an nitride/oxide film negative image of the desired pattern.

The pathways are formed in the surfaces of the wafers by etching the silicon, using either isotropic or anisotropic etchant, the choice of which is dependent on the shape of the pathway desired. Curved shapes are etched using an isotropic etchant. Straight shapes may employ either etchant, depending on the desired cross-sectional shape pathway. If a trapezoidal cross-section is desired an anisotropic etchant is used.

If a given wafer is to be etched on both major surfaces using the same etchant, both sides of the wafer may be masked with resist, the resist exposed with the desired pattern on each surface, developed, washed and the nitride/oxide etched simultaneously on both surfaces. Then the silicon may be simultaneously etched on both surfaces. If different types of etchants are to be used on each side of the wafer, all steps for the first etchant are completed and then the steps are repeated for the second etchant. After all the etching steps have been completed the vertical passages or vias through the wafer are formed by laser cutting through the wafers, typically using a pulsed neodymium-YAG laser cutting system. After laser cutting, the wafers are again recleaned to remove cutting debris. The remaining nitride layer of the negative image is removed from the wafer, by using a suitable solvent, such as boiling phosphoric acid, exposing the undamaged oxide layer. The remaining oxide layer negative image may optionally be removed from the wafer, by using a suitable solvent, such as buffered hydrogen fluoride. The wafer is recleaned, using the technique as described above.

Wafers or plates of the outer group of laminae are fabricated, using techniques which are dependent upon the lamina material. Outer laminae which are comprised of group III, IV or V material are processed using etching, grinding, drilling and polishing techniques similar to those of the inner laminae. Outer laminae comprised of borosilicate glass, or fused silica are fabricated using conventional glass cutting, drilling, grinding, and polishing techniques.

When all the wafers have been individually processed the wafers of the inner group are carefully stacked in a precisely aligned manner and fusion bonded. To achieve good bonding, the surfaces should be highly planar and the oxide layers on each surface should be undamaged. Since silicon is somewhat transparent in the infrared, a microscope with an infrared video camera may be used, with optional alignment indicia on each wafer, to insure precise alignment of the wafers before they are fusion bonded. If a lamina of the outer group is comprised of glass, this lamina is then anodically bonded, one at a time, to the fused stack of inner laminae.

The following example illustrates the evaluation of an experimental apparatus for the gas-phase photo-chlorination of DCDMS to dichloro(chloro-methyl)methyl-silane (DCCMMS). The DCDMS photoreaction is carried out according to well understood chemistry as is readily appreciated by those skilled in the art. The DCDMS photoreaction is commercially carried out in a liquid phase reaction. Operations of this reaction have resulted in explosive mixtures. Safety considerations, therefore, are primary concerns in this reaction.

The apparatus, comprised of three wafers, had 10 high speed mixers and a spiral photoreactor channel (similar to that of FIG. 15) etched into the silicon substrate. Spiral channels of 250 microns deep and a width of 3 mm and a length of 1900 mm were formed (via an isotropic etching technique for the creation of the photochamber channels). Pressure drops through the experimental apparatus were 5 psi. Precision laser drilling was used to form vias between silicon wafer layers, which were then fusion bonded together, and anodic bonding of borosilicate glass to silicon was used to create the "window" for the photochamber.

The experimental apparatus was clamped on a heated plate which maintained the temperature of the apparatus at 100 degrees Celsius. DCDMS at 2.7 grams per minute and chlorine gas at a mole ratio of 1:10 were introduced to the apparatus at the inlet ports. The apparatus converted 7.6% of the chlorine at a yield of 98.6% to DCCMMS. Examination of the silicon surfaces exposed to the reaction mass revealed no apparent chemical attack.

These results demonstrate that the potentially hazardous reaction can be run safely and obtain similar yield performance, (at similar conversion percentages and far lower residence time in the photoreactor) to that of the conventional process.

Those skilled in the art, having the benefit of the teachings of the present invention as hereinabove set forth, can effect numerous modifications thereto. It is readily appreciated that such modifications can be made without departing from the spirit of the scope of the present invention. Accordingly, such modifications are to be construed as being encompassed within the scope of the present invention as set forth in the appended claims.

What is claimed is:

1. A process for the preparation of an integral structure for chemical processing and manufacture comprising:
    (a) processing a plurality of laminae each having a top portion and a bottom portion and a desired thickness, sufficient to form desired channels thereon or therethrough, said channels thereon being continuous along one or more laminae and discontinuous along one or more other laminae;
    (b) stacking and bonding said laminae together in precise alignment with at least one inlet port and at least one outlet port formed therein for the receipt and discharge of chemicals, and wherein said continuous and discontinuous channels are precisely aligned between adjacent laminae to form at least one continuous three-dimensionally tortuous channel therethrough for accommodating chemicals to be processed, said channel connected to said inlet and outlet ports, and said laminae comprising a material selected for compatibility with the chemical process; and
    (c) positioning one or more means to perform at least one unit operation to cooperate with said channel and to effect a desired control so that the chemicals are processed.

2. The process of claim 1 wherein said laminae further comprise a material selected from the group consisting of nonmetallic elements of groups III, IV, and V of the Periodic Table, ceramics, glasses, polymers, composite materials, and metals.

3. The process of claim 2 wherein said laminae further comprise a material selected from the group consisting of groups III, IV and V of the Periodic Table.

4. The process of claim 3 wherein said laminae further comprise a material selected from group IVA of the Periodic Table.

5. The process of claim 4, wherein said laminae further comprise a material selected from the group consisting of silicon and germanium.

6. The process of claim 2, wherein said laminae further comprise a ceramic selected from the group consisting of silicon carbide, sapphire, and alumina.

7. The process of claim 1 wherein said processing (a) is performed by a procedure selected from the group consisting of subtractive processes, additive processes, and forming processes.

8. The process of claim 7 wherein said subtractive process is selected from the group consisting of chemical etching, electrochemical machining, electrical discharge machining, laser ablation, drilling and cutting, abrasive grinding and single diamond point cutting.

9. The process of claim 7 wherein said additive process is selected from the group consisting of electroforming, selective plating, chemical vapor deposition, stereo lithographic photoforming and welding.

10. The process of claim 7 wherein said forming process is selected from the group consisting of molding, casting, and stamping.

* * * * *